(12) United States Patent
Shobayashi

(10) Patent No.: US 11,590,009 B2
(45) Date of Patent: Feb. 28, 2023

(54) STENT

(71) Applicant: Yasuhiro Shobayashi, Tokyo (JP)

(72) Inventor: Yasuhiro Shobayashi, Tokyo (JP)

( * ) Notice: Subject to any disclaimer, the term of this patent is extended or adjusted under 35 U.S.C. 154(b) by 0 days.

(21) Appl. No.: 17/753,584

(22) PCT Filed: Aug. 11, 2021

(86) PCT No.: PCT/JP2021/029676
§ 371 (c)(1),
(2) Date: Mar. 8, 2022

(87) PCT Pub. No.: WO2022/034905
PCT Pub. Date: Feb. 17, 2022

(65) Prior Publication Data
US 2022/0265447 A1  Aug. 25, 2022

(30) Foreign Application Priority Data

Aug. 12, 2020 (JP) .............................. JP2020-136261

(51) Int. Cl.
*A61F 2/90* (2013.01)
*A61F 2/89* (2013.01)
(Continued)

(52) U.S. Cl.
CPC .................. *A61F 2/90* (2013.01); *A61F 2/89* (2013.01); *A61F 2/915* (2013.01); *A61F 2002/825* (2013.01)

(58) Field of Classification Search
CPC ...... A61F 2/86; A61F 2/89; A61F 2/90; A61F 2/915; A61F 2002/825; A61F 2002/91508; A61F 2002/91583
See application file for complete search history.

(56) References Cited

U.S. PATENT DOCUMENTS 5,948,016 A    9/1999  Jang
2002/0038145 A1*  3/2002  Jang .......................... A61F 2/91
                                                         623/1.42
(Continued)

FOREIGN PATENT DOCUMENTS

JP    2010-535075 A    11/2010
JP    2013-517913 A     5/2013
(Continued)

OTHER PUBLICATIONS

International Search Report issued in PCT/JP2021/029676; dated Oct. 26, 2021.
(Continued)

*Primary Examiner* — Dinah Baria
(74) *Attorney, Agent, or Firm* — Studebaker & Brackett PC

(57) ABSTRACT

A stent 10 includes corrugated pattern bodies 11 and connection elements 12. A corrugated pattern is formed of corrugated units 14, corrugated unit 14 including a first stem 15, a second stem 16, a third stem 17, a first top portion 18 coupling a first end portion 15a of the first stem 15 and a first end portion 16a of the second stem 16, and a second top portion 19 coupling a second end portion 16b of the second stem 16 and a first end portion 17a of the third stem 17. A second end portion 17b of the third stem 17 is connected to a second end portion 15b of the first stem 15 in another corrugated unit adjacent to corrugated unit. A first end portion 12a of connection element 12 is connected to the first top portion 18 of one of adjacent ones of the corrugated units 14, and a second end portion 12b of connection element 12 is connected to the second end portion 15b of the other one of the adjacent ones of the corrugated units 14.

6 Claims, 30 Drawing Sheets

(51) Int. Cl.
    *A61F 2/915*     (2013.01)
    *A61F 2/82*     (2013.01)

(56) References Cited

U.S. PATENT DOCUMENTS

| | | | |
|---|---|---|---|
| 2009/0024205 | A1 | 1/2009 | Hebert et al. |
| 2016/0015541 | A1 | 1/2016 | Shobayashi |
| 2017/0100268 | A1 | 4/2017 | Shobayashi |
| 2019/0201218 | A1* | 7/2019 | Shobayashi .............. A61F 2/89 |

FOREIGN PATENT DOCUMENTS

| | | |
|---|---|---|
| WO | 2009/017827 A1 | 2/2009 |
| WO | 2012/145106 A1 | 10/2012 |
| WO | 2015/125320 A1 | 8/2015 |
| WO | 2015/145596 A1 | 10/2015 |

OTHER PUBLICATIONS

Written Opinion of the International Searching Authority issued in PCT/JP2021/029676 dated Oct. 26, 2021.

* cited by examiner

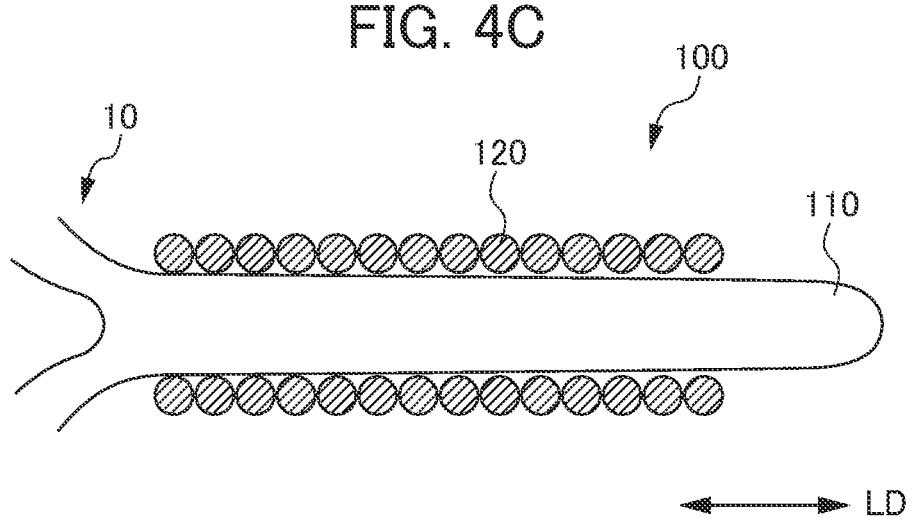

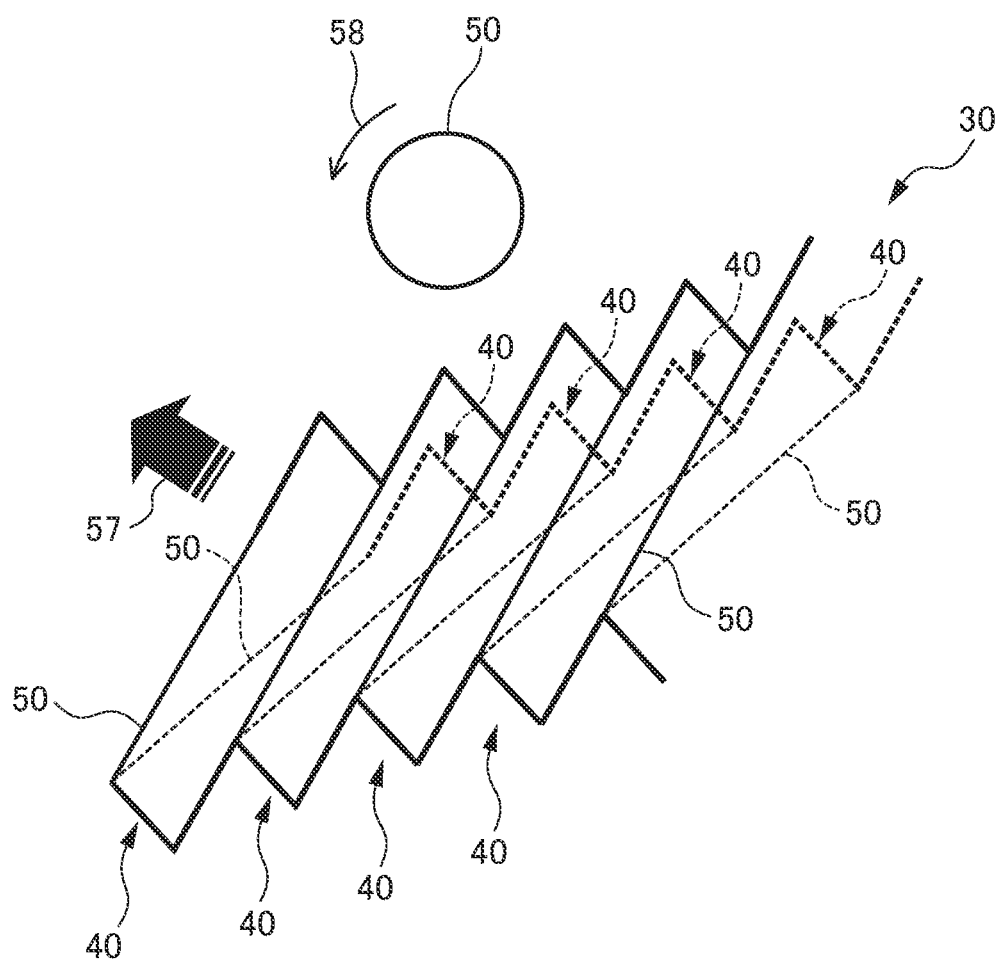

STENT

TECHNICAL FIELD

The present invention relates to a stent to be implanted in a lumen structure of a biological body to expand a lumen.

BACKGROUND ART

In a case where stenosis occurs in a biological organ having a lumen structure, such as a blood vessel, trachea, or intestine, a net-shaped cylindrical stent is used for ensuring the patency of a lesion area by expansion of an inner cavity at the location where the stenosis occurs. In many cases, the above-described biological organ partially has a bent or tapered structure (i.e., a tubular structure in which an inner cavity sectional diameter varies according to location in an axial direction). There has been a demand for a stent with a high conformability, i.e., a stent flexibly applicable to such a complicated blood vessel structure. In recent years, a stent has been applied to brain blood vessel treatment. The cerebrovascular system has a complicated structure among hollow organs. The cerebrovascular system has many bent areas and many areas with tapered structures. For this reason, a stent needs to have a particularly high conformability.

A stent structure is generally roughly classified into two types, namely, an open cell type and a closed cell type. A stent with the open cell structure exhibits extremely-flexible mechanical properties in a longitudinal axis direction, and therefore, has been considered as having a high conformability and an effective stent structure for placing the stent in a bent hollow organ. However, there is a probability that in such a stent with the open cell structure, some struts of the stent project in a flare shape to the outside of the stent in a radial direction upon bending, and for this reason, there is a risk that tissue of a hollow organ of a biological body, such as a blood vessel, may become damaged when the stent is implanted therein. On the other hand, there are stents with the closed cell structure that allow partial intraoperative stent reimplantation or complete intraoperative stent reimplantation which is difficult to achieve with stents with the open cell structure.

Although the stents with the closed cell structure described above do not have the same risk of the stent struts protruding outwards in the radial direction as the stents with the open cell structure, the stents with the closed cell structure tend to lack conformability due to their structure. To solve these problems, a spiral stent has been proposed as a technique relating to a stent having a closed cell structure and exhibiting high flexibility (see, e.g., Patent Document 1). The stent of Patent Document 1 includes, in an open state, spiral annular bodies having a corrugated pattern and coil-shaped elements connecting the annular bodies adjacent to each other.

Patent Document 1: Japanese Unexamined Patent Application (Translation of PCT Application), Publication No. 2010-535075

DISCLOSURE OF THE INVENTION

Problems to be Solved by the Invention

Two types of mechanical flexibility in an axial direction (an axis direction, a center axis direction) and a radial direction (a direction perpendicular to the axial direction) of a stent are important for achieving a stent with high conformability. Flexibility in the axial direction means stiffness against bending along the axial direction or the easiness of bending, and is a property necessary for flexibly bending a stent along the axial direction in accordance with a bent area of a hollow organ of a biological body. On the other hand, flexibility in the radial direction means stiffness against expansion/contraction in the direction perpendicular to the axial direction or the easiness of expansion/contraction, and is a property necessary for flexibly changing the radius of a stent along the shape of an outer wall of a lumen structure of a hollow organ of a biological body such that the stent closely contacts the outer wall of the lumen structure.

The stent including the spiral annular bodies having the corrugated pattern and the coil-shaped elements connecting these annular bodies as in Patent Document 1 above has a higher conformability than that of a typical closed cell-type stent. However, in the cell structure of the stent of Patent Document 1, when the bending radius decreases to some extent, a phenomenon called "kink" occurs. The kink means that a twist/bend occurs in a section of the stent and the stent section deforms to a substantially oval shape. If a kink occurs in a stent implanted in a bent hollow organ, there is a possibility that a gap between an inner wall of the hollow organ and the stent becomes clogged with a blood clot and flow of liquid such as blood in the hollow organ becomes obstructed. For this reason, not only the conformability but also retention of a circular sectional shape upon bending have been demanded for a stent. In description below, the degree of retention of the circular sectional shape upon bending of the stent is referred to as "patency".

An object of the present invention is to provide a stent having a high patency against bending.

Means for Solving the Problems

The present invention relates to a stent to be inserted into a catheter while being compressed radially, the stent including a plurality of corrugated pattern bodies having a corrugated pattern and arranged next to each other in an axial direction, and a plurality of connection elements arranged in a direction about an axis and connecting the corrugated pattern bodies adjacent to each other. The corrugated pattern is formed of a plurality of corrugated units, each corrugated unit including a first stem, a second stem, a third stem, a first top portion coupling a first end portion of the first stem on one side (first side) and a first end portion of the second stem on one side (first side), and a second top portion coupling a second end portion of the second stem on the other side (second side) and a first end portion of the third stem on one side (first side). A second end portion of the third stem on the other side (second side) is connected to a second end portion of the first stem on the other side (second side) in another one of the corrugated units adjacent to each corrugated unit in the direction about the axis. A first end portion of each connection element on one side (first side) is connected to the first top portion of one of adjacent ones of the corrugated units in the axial direction, and a second end portion of each connection element is connected to the second end portion of the first stem of the other one of the adjacent ones of the corrugated units in the axial direction.

In the above-described aspect of the invention, the second top portion of each corrugated unit may be formed to protrude toward a distal side in the direction of insertion of the stent into the catheter.

In the above-described aspect of the invention, the third stem of one of the corrugated units and the first stem of another one of the corrugated units adjacent to the one of the corrugated units in the direction about the axis may be, at end portions thereof, coupled to each other to form a slit therebetween.

In the above-described aspect of the invention, when viewed in a radial direction perpendicular to the axial direction, an annular direction of the corrugated pattern of each corrugated pattern body may be inclined with respect to the radial direction.

In the above-described aspect of the invention, the sum of the length of the first stem and the length of the second stem may be longer than the length of the third stem.

In the above-described aspect of the invention, the sum of the length of the first stem and the length of the second stem may be shorter than the length of the third stem.

In the above-described aspect of the invention, the length of each connection element may be shorter than the length of the second stem, and when viewed in the radial direction perpendicular to the axial direction, the annular direction of the corrugated pattern of each corrugated pattern body may be substantially coincident with the radial direction.

Effects of the Invention

According to the present invention, a stent with a high patency against bending can be provided.

BRIEF DESCRIPTION OF THE DRAWINGS

FIG. 4C is a sectional view of the marker 100;

FIG. 14 is a schematic view showing the state of continuous cells 40 in a back-side region of the bent stent 30 when the stent 30 is virtually opened in the planar shape;

PREFERRED MODE FOR CARRYING OUT THE INVENTION

Figure 1:
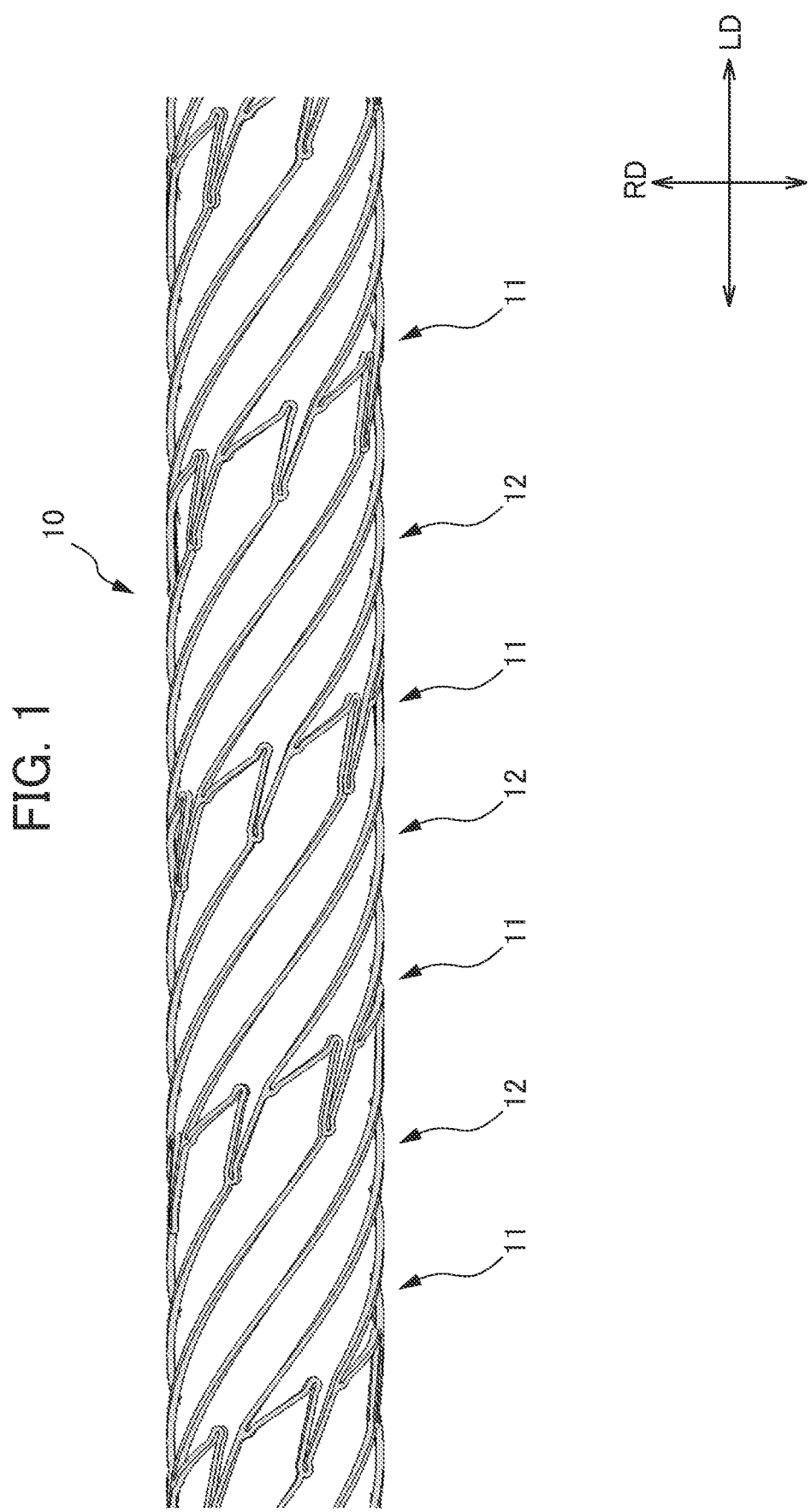
FIG. 1 is a side view showing the configuration of a stent 10 of a first embodiment.

Hereinafter, an embodiment of a stent according to the present invention will be described. Note that any of the drawings attached to the present specification shows a schematic view and the shape, scale, longitudinal-lateral dimensional ratio, etc. of each portion are changed or exaggerated as compared to actual shape, scale, longitudinal-lateral dimensional ratio, etc. for the sake of easy understanding of the drawings. Moreover, in the drawings, hatching showing the cross-section of members has been omitted where appropriate. In the present specification, terms specifying shapes, geometric conditions, and the degrees thereof, such as "parallel" and "direction", include not only exact meanings of these terms, but also ranges taken as being substantially parallel and being substantially in a direction.

First Embodiment

Figure 2:
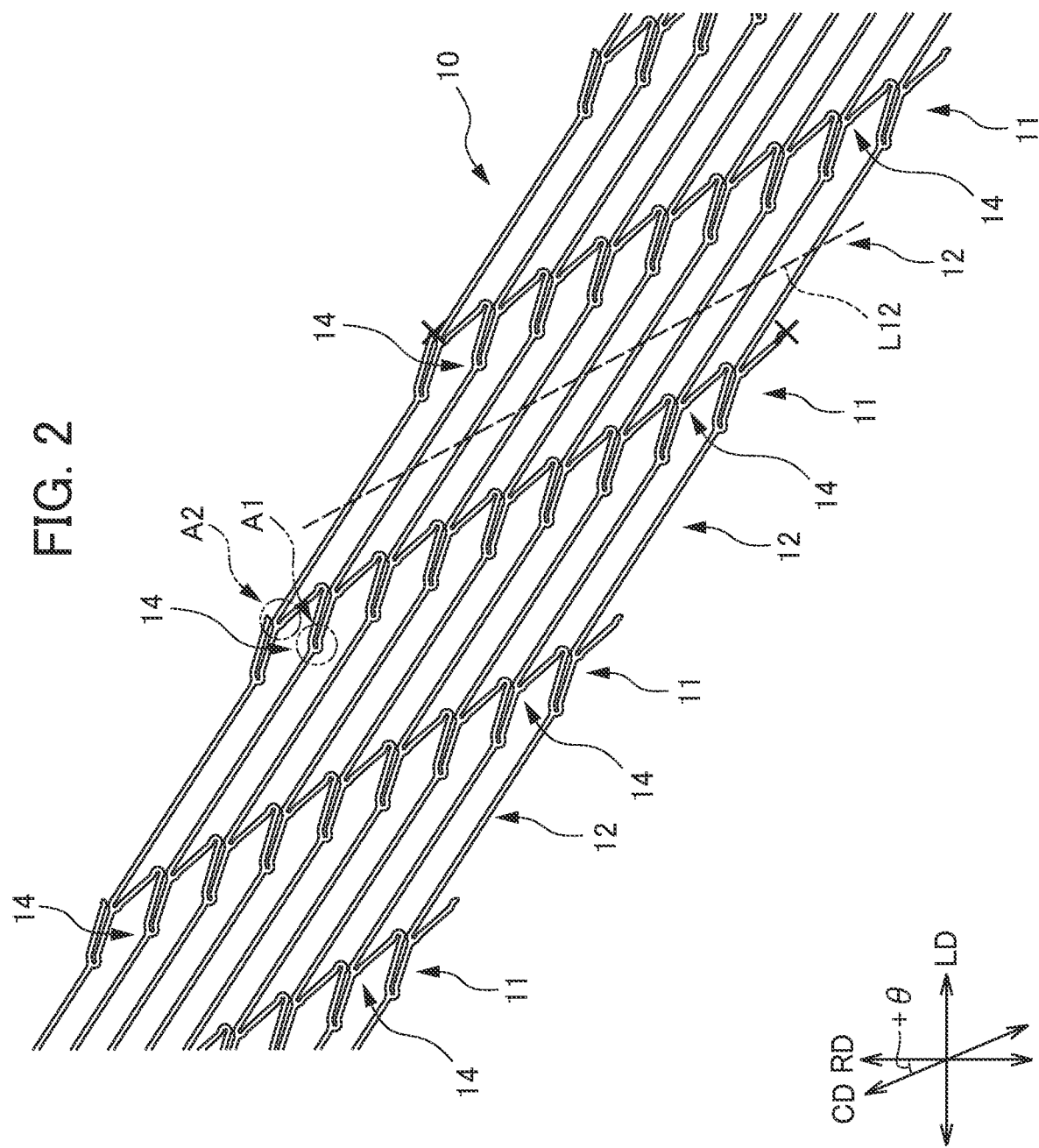
FIG. 2 is a development view showing a state in which the stent 10 is virtually opened in a planar shape.
Figure 3:
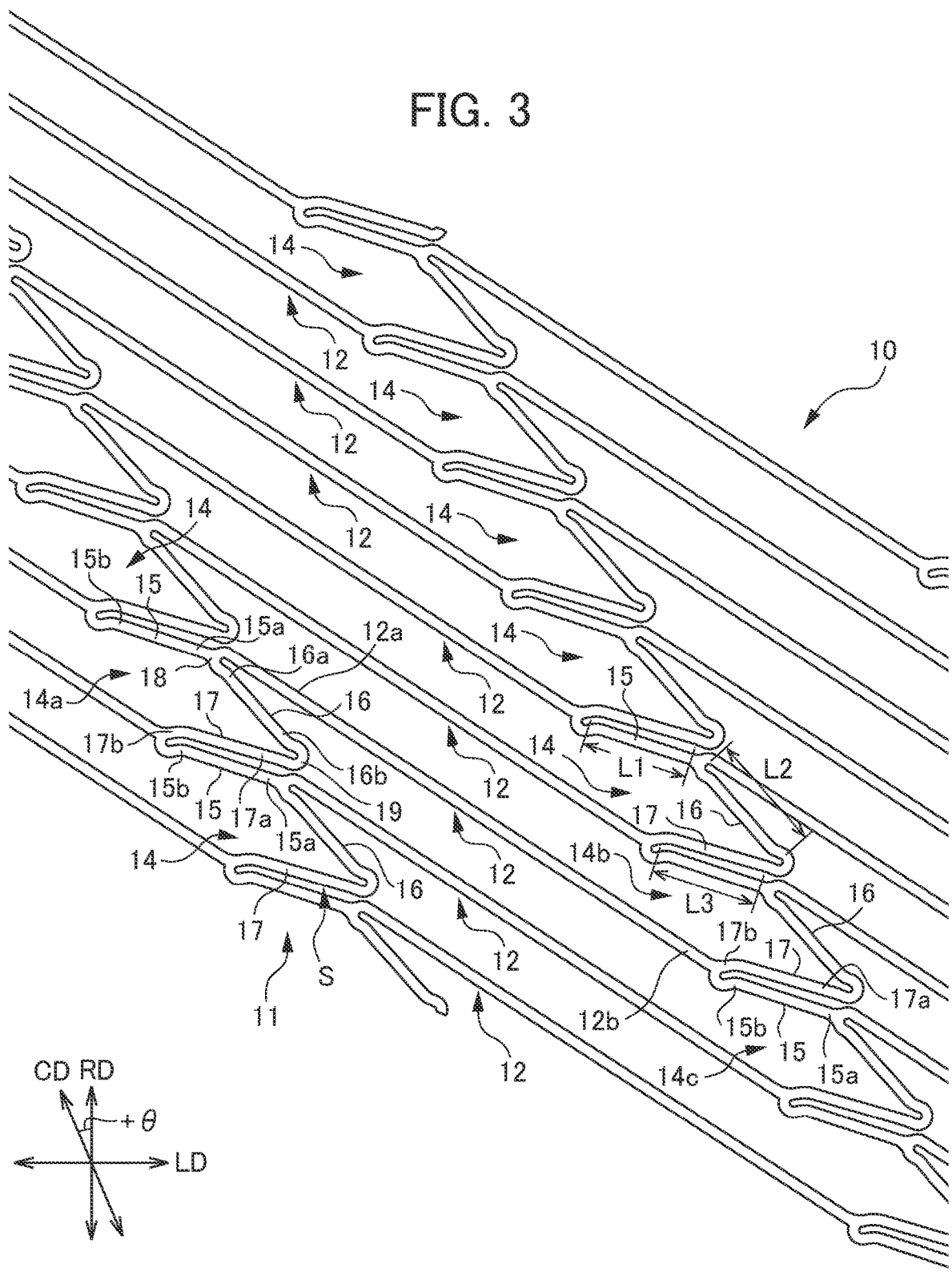
FIG. 3 is a partially-enlarged view of the stent 10.
Figure 4A:
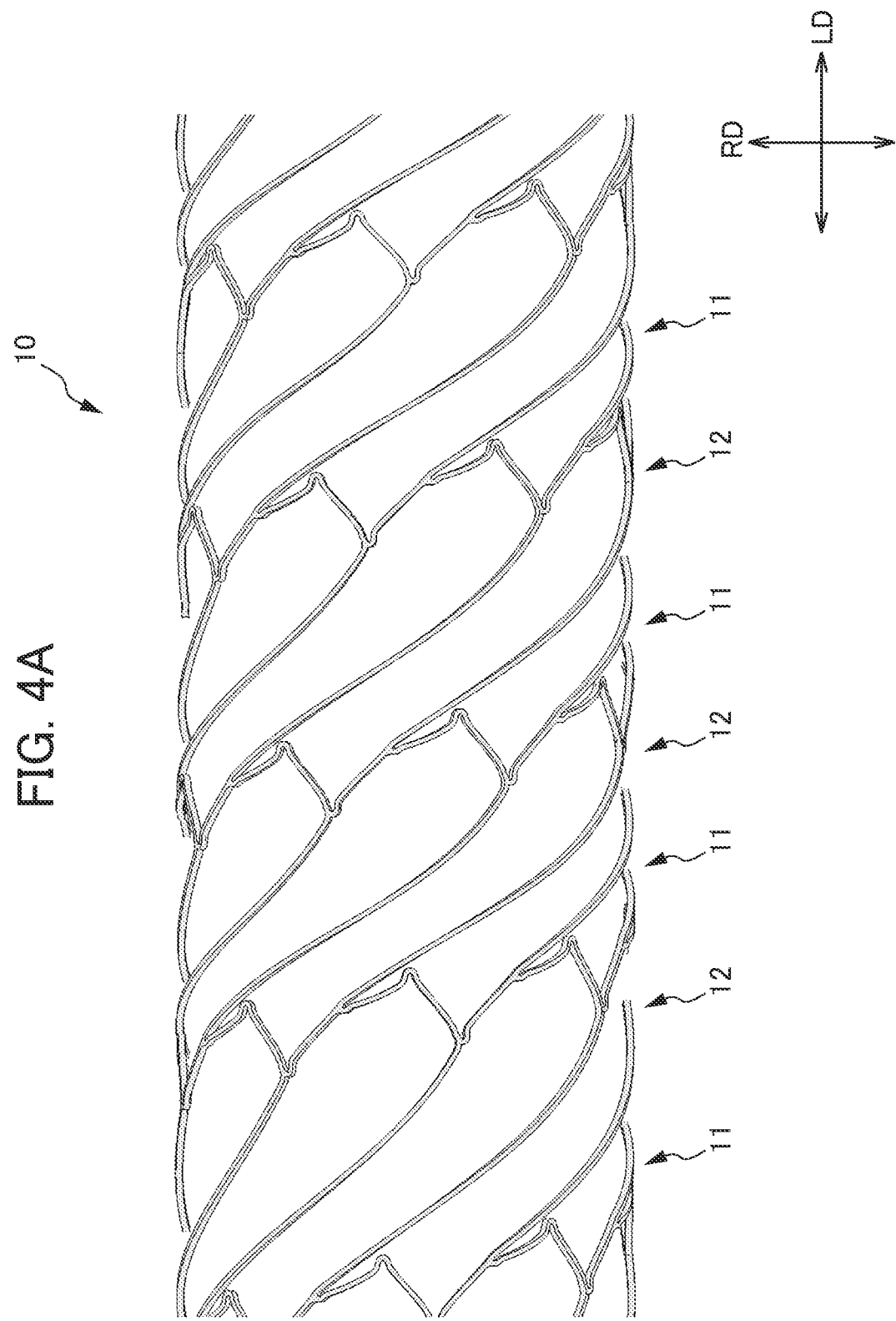
FIG. 4A is a side view showing a state in which the diameter of the stent 10 is expanded.
Figure 4B:
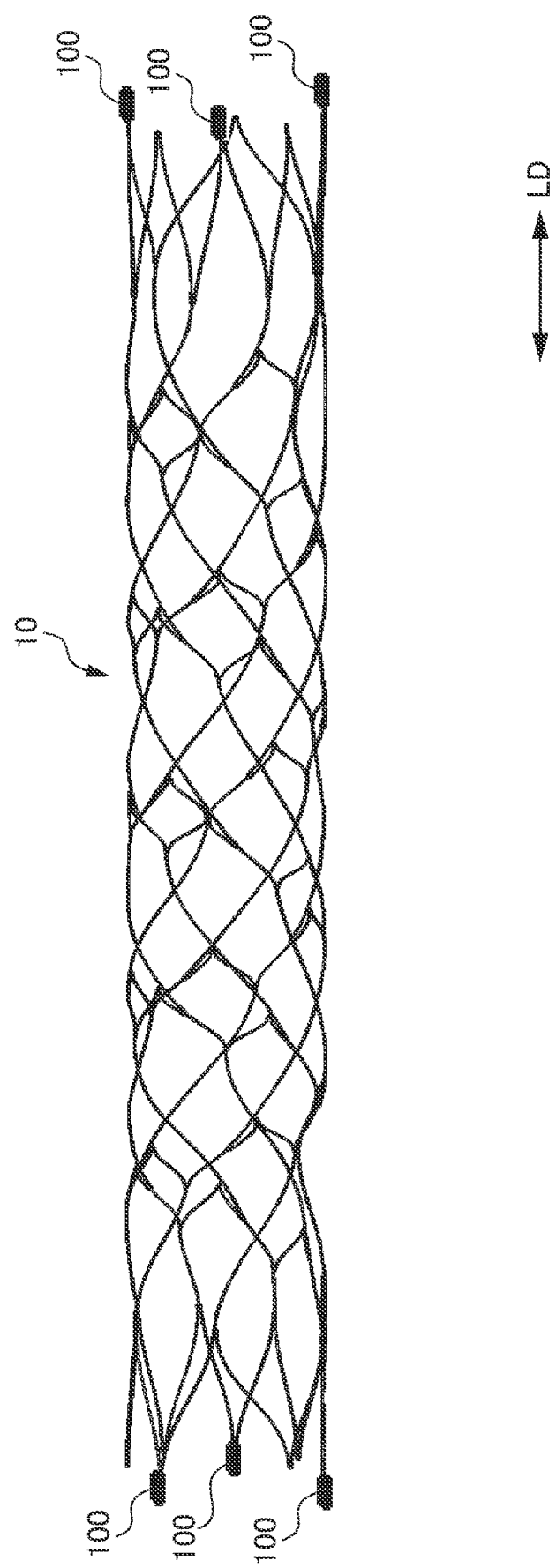
FIG. 4B is a side view of the stent 10 provided with markers 100.
Figure 5A:
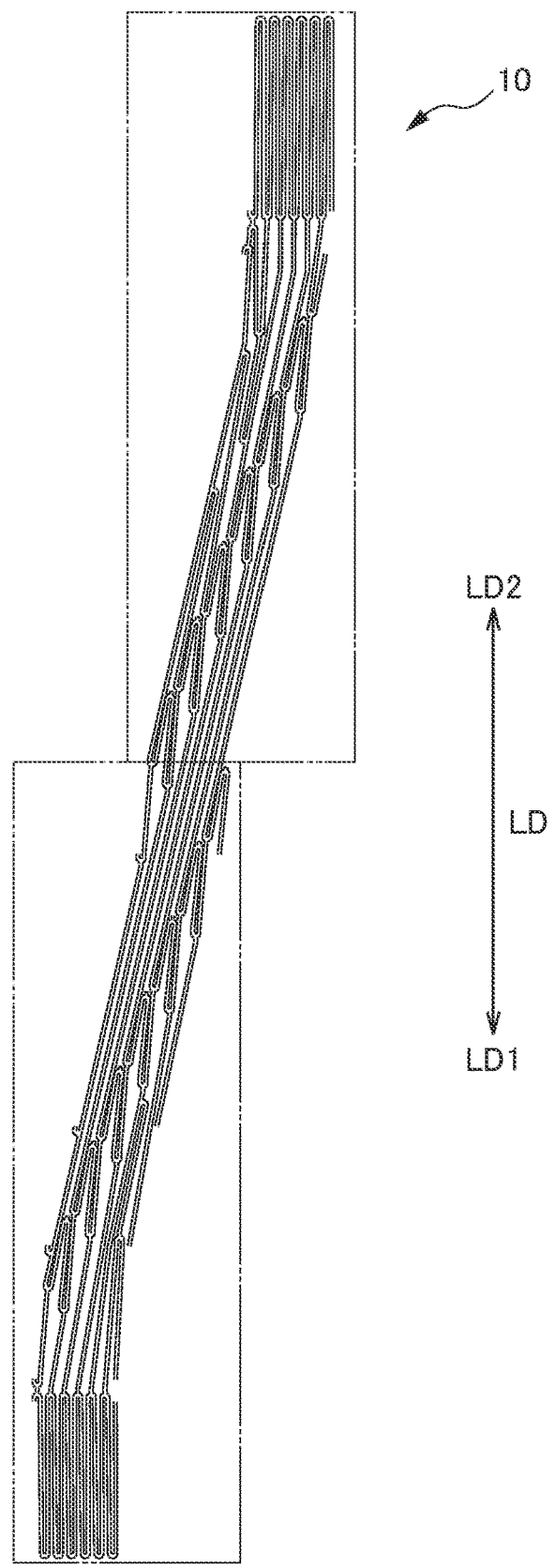
FIG. 5A is a view for describing the direction of protrusion of a second top portion 19 in the stent 10.
Figure 5B:
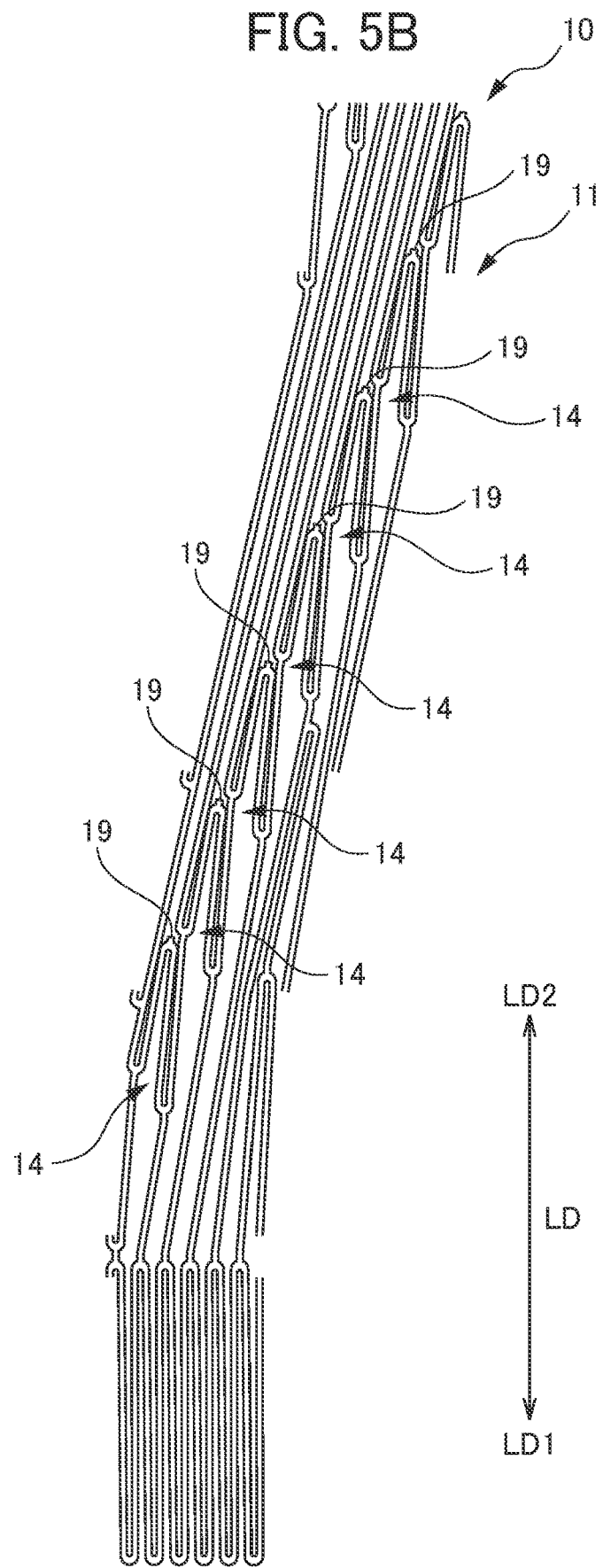
FIG. 5B is a view for describing the direction of protrusion of the second top portion 19 in the stent 10.
Figure 5C:
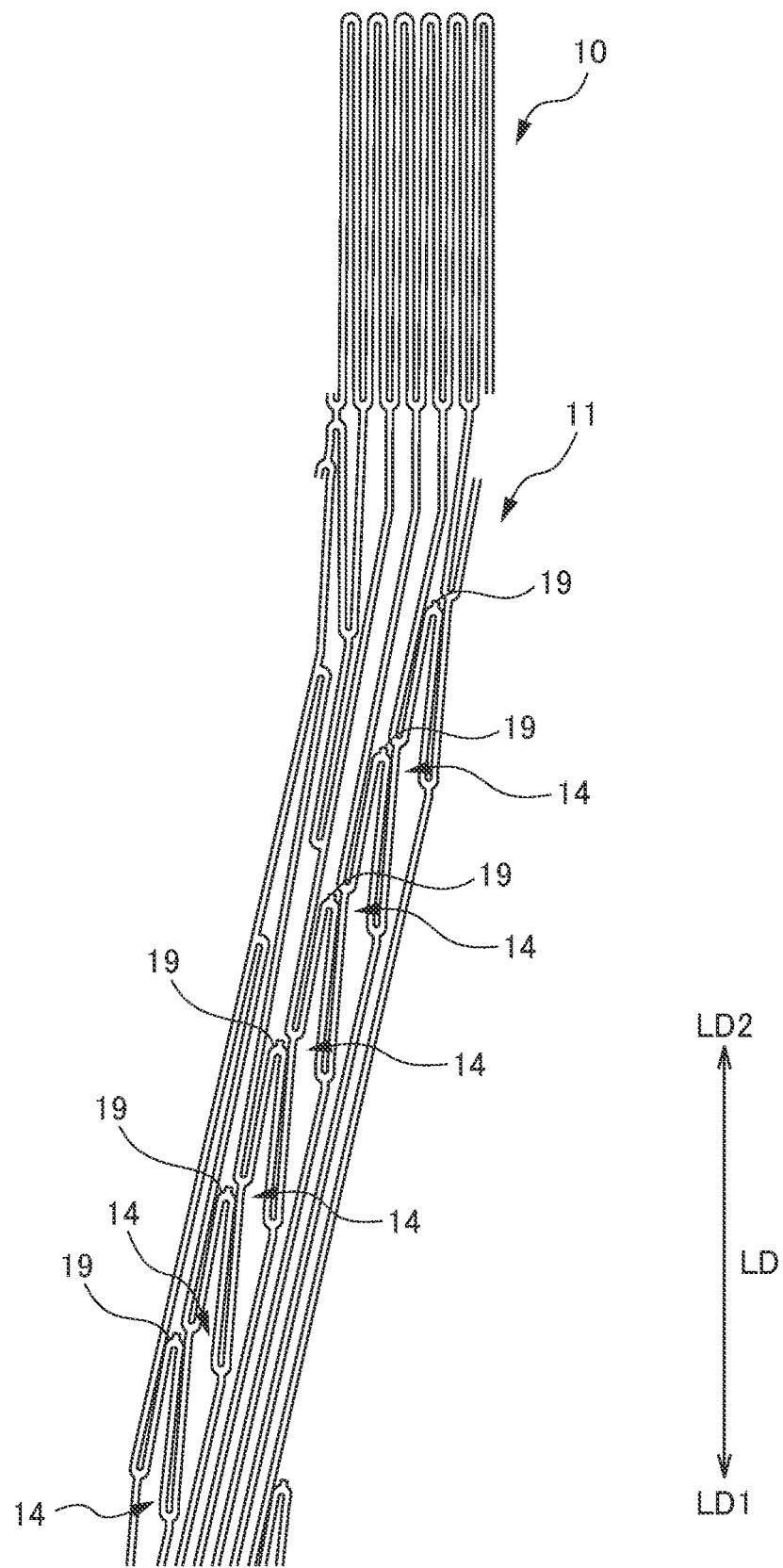
FIG. 5C is a view for describing the direction of protrusion of the second top portion 19 in the stent 10.

FIG. 1 is a side view showing the configuration of a stent 10 of a first embodiment. FIG. 2 is a development view showing a state in which the stent 10 shown in FIG. 1 is virtually opened in a planar shape. FIG. 3 is a partially-enlarged view of the stent 10 shown in FIG. 2. FIG. 4A is a side view showing a state in which the diameter of the stent 10 shown in FIG. 1 is expanded. FIG. 4B is a side view of the stent 10 provided with markers 100. FIG. 4C is a sectional view of the marker 100. FIGS. 5A to 5C are views for describing a protruding direction of a second top portion 19 of the stent 10.

As shown in FIG. 1, the stent 10 is in a substantially cylindrical shape. A peripheral wall of the stent 10 has such a mesh pattern structure that a plurality of cells surrounded by a wire-like material and having the same shape spreads in a circumferential direction. For the sake of easy understanding of the structure of the stent 10, FIG. 2 shows the state in which the stent 10 is opened in the planar shape. Moreover, FIG. 2 virtually shows, for the sake of simplicity in the mesh pattern, such a shape that the mesh pattern is repeated as compared to an actual open state. In the present specification, the "peripheral wall" of the stent 10 means a portion dividing the inside and outside of a cylinder of a substantially cylindrical structure of the stent 10 from each other. The "cell" is also called an opening or a compartment, and means a portion surrounded by the wire-like material forming the mesh pattern of the stent 10. A "strut" means each of stems 15 to 17, a connection element 12 (described later), etc. formed of the above-described wire-like material.

As the material of the stent 10, a material itself having a high stiffness and a high biological compatibility is preferred. Examples of such a material include titanium, nickel, stainless steel, platinum, gold, silver, copper, iron, chromium, cobalt, aluminum, molybdenum, manganese, tantalum, tungsten, niobium, magnesium, calcium, and alloy containing these materials. Particularly, the stent 10 is preferably made of a material having superelastic properties, such as nickel titanium (Ni—Ti) alloy. The stent 10 shown in FIG. 1 may be produced in such a manner that a substantially-cylindrical thin tube made of the above-described material is processed with a laser.

As the material of the stent 10, synthetic resin materials such as polyolefin including PE and PP, polyamide, polyvinyl chloride, polyphenylene sulfide, polycarbonate, polyether, and polymethylmethacrylate may be also used. Further, biodegradable resins (biodegradable polymers) such as polylactate (PLA), polyhydroxybutyrate (PHB), polyglycolic acid (PGA), and poly(ε-caprolactone) may be also used. Of these materials, titanium, nickel, stainless steel, platinum, gold, silver, copper, magnesium, or alloy containing these materials are preferred. Examples of such alloy include Ni—Ti alloy, Cu—Mn alloy, Cu—Cd alloy, Co—Cr alloy, Cu—Al—Mn alloy, Au—Cd—Ag alloy, Ti—Al—V alloy, and alloy of magnesium and Zr, Y, Ti, Ta, Nd, Nb, Zn, Ca, Al, Li, Mn, or the like. In addition to the materials described above, non-biodegradable resins may be used as the material of the stent 10. As described above, any material may be used to form the stent 10 as long as such a material has a biological compatibility.

The stent 10 may contain a medical agent. The stent 10 containing the medical agent as described herein means that the stent 10 releasably carries the medical agent so as to dissolve out the medical agent. Although the medical agent is not limited, a physiologically active substance may be used, for example. Examples of the physiologically active substance include a medical agent for inhibiting intima thickening, a carcinostatic, an immunosuppressant, an antibiotic, an antirheumatic, an antithrombotic, an HMG-CoA reductase inhibitor, an ACE inhibitor, a calcium channel blocker, an antilipemic, an anti-inflammatory, an integrin inhibitor, an antiallergic, an antioxidant, a GPIIbIIIa antagonist, retinoid, flavonoid, carotenoid, a lipid improver, a DNA synthesis inhibitor, a tyrosine kinase inhibitor, an antiplatelet, a vascular smooth muscle growth inhibitor, an anti-inflammatory agent, and interferon, and these medical agents may be used in combination.

Particularly, the medical agent for inhibiting intima thickening for preventing restenosis is preferred, and includes, for example, a medical agent having intima thickening inhibitory action not blocking endothelial cell growth. Examples of such a medical agent include argatroban ((2R,4R)-4-methyl-1-[N2-((RS)-3-methyl-1,2,3,4-tetrahydro-8-quinolinesulfonyl)-L-arginyl]-2-piperidinecarboxylic acid (Japanese Unexamined Patent Application, Publication No. 2001-190687; PCT International Publication No. WO 2007/058190)), ximelagatran, melagatoran, dabigatran, dabigatran etexilate, rapamycin, everolimus, biolimus A9, zotarolimus, tacrolimus, paclitaxel, and statin.

For forming the stent 10 containing the medical agent, the surface of the stent 10 may be coated with the medical agent, for example. In this case, the surface of the stent 10 may be directly coated with the medical agent, or may be coated with a polymer containing the medical agent. Alternatively, e.g., a groove or a hole for storing the medical agent may be provided as a reservoir at the stent 10, and the medical agent or the mixture of the medical agent and polymer may be stored in such a reservoir. The reservoir for storage is, for example, described in Japanese Unexamined Patent Application, Publication (Translation of PCT Application) No. 2009-524501. Polymer to be used in this case includes, for example, soft polymer whose glass-transition temperature (Tg) is −100° C. to 50° C., such as silicone rubber, urethane rubber, fluorine resin, polybutyl acrylate, polybutyl methacrylate, acrylic rubber, natural rubber, ethylene-vinyl acetate copolymer, styrene-butadiene block copolymer, styrene-isoprene block copolymer, and styrene-isobutylene block copolymer; and biodegradable polymer such as polylactate, poly(lactic acid-glycolic acid), polyglycolic acid, poly(lactic acid-ε-caprolactone), poly(glycolic acid-trimethylene carbonate), and poly-β-hydroxybutyric acid. For example, polymer and the medical agent may be mixed in such a manner that the medical agent is dispersed in polymer according to description in PCT International Publication No. WO 2009/031295. The medical agent contained in the stent 10 is delivered to an affected area through the stent 10, and in such an area, the stent 10 sustained-releases the medical agent. The surface of the stent 10 may be coated with a carbon-based material such as diamond-like carbon (DLC, F-DLC).

In a case where the stent 10 shown in FIG. 1 is produced from, e.g., a superelastic alloy tube, a tube having a diameter of about 2 to 3 mm is processed with a laser, and thereafter, is stretched in a radial direction until the diameter reaches about 5 mm. FIG. 2 shows the state in which the stent 10 not stretched yet after a tube with a diameter of 2 mm has been processed with a laser is virtually opened in the planar shape. Moreover, FIG. 4A shows the state in which the diameter of the stent 10 shown in FIG. 1 is expanded to 5 mm. The diameter of the stent 10 is narrowed in the radial direction from the state shown in FIG. 4A, and thereafter, the stent 10 is housed (inserted) in an inner cavity of a catheter (not shown). The shape shown in FIG. 4A is recovered in such a manner that the stent 10 housed in the catheter is pushed out. The stent 10 is made of an elastic material such as superelastic alloy or shape-memory alloy so that the above-described shape recovery function can be obtained. Note that production of the stent 10 is not limited to processing with a laser, and for example, the stent 10 may be also produced by other methods such as cutting.

The markers 100 may be provided on both end sides of the stent 10 in an axial direction LD. FIG. 4B shows such a configuration that the markers 100 are provided on both end sides of the diameter-expanded stent 10 of FIG. 4A in the axial direction LD. The marker 100 is a member serving as a mark for checking the position of the stent 10 in a hollow organ such as a blood vessel, and is made of a radiopaque material. As shown in FIG. 4C, the marker 100 includes a tip end portion 110 of the stent 10 and a coil-shaped spring 120 provided outside the tip end portion 110. A tip end of the tip end portion 110 of the stent 10 protrudes from the coil-shaped spring 120. The coil-shaped spring 120 is preferably made of a material through which radiation such as an X-ray cannot pass and which can be formed in a coil shape. Examples of the material of the coil-shaped spring 120 include platinum-iridium (Pt—Ir).

The method for joining the coil-shaped spring 120 and the tip end portion 110 of the stent 10 to each other is not particularly limited as long as such a method is used for medical equipment joint such as welding, bonding with UV, or silver brazing. The welding method includes, for example, a method in which the coil-shaped spring 120 and the tip end portion 110 of the stent 10 are melted by welding to bond and fix the coil-shaped spring 120 and the tip end portion 110 to each other, and a method in which the region of the tip end portion 110 of the stent 10 protruding from the coil-shaped spring 120 is melted to restrict movement of the coil-shaped spring 120.

In the case of bonding with UV, the coil-shaped spring 120 is fixed to the tip end portion 110 of the stent 10 by means of medical-grade radiation curable polymer. The steps of such a method are as follows: the tip end portion 110 of the stent 10 is coated with a curable polymer solution, the coil-shaped spring 120 is placed thereon, and thereafter, these portions are irradiated with radiation to cure the curable polymer solution to fix the coil-shaped spring 120 to the tip end portion 110 of the stent 10. In the case of silver brazing, the coil-shaped spring 120 is made of a material different from that of the stent 10, and the coil-shaped spring 120 is fixed to the tip end portion 110 of the stent 10 in such a manner that, e.g., silver solder soaks into the coil-shaped spring 120 from above.

As shown in FIGS. 1 to 3, the stent 10 of the first embodiment includes a plurality of annular bodies (corrugated pattern bodies) 11 arranged next to each other in the axial direction (a longitudinal axis direction, a center axis direction) LD and a plurality of connection elements 12 connecting the annular bodies 11 adjacent to each other in the axial direction LD. As described later, when the stent 10 is viewed in a radial direction RD perpendicular to the axial direction LD, an annular direction CD of the annular body 11 is inclined with respect to the radial direction RD. The angle +θ of inclination of the annular direction CD of the annular body 11 with respect to the radial direction RD is 30 to 60 degrees, for example.

As shown in FIG. 2, the annular body 11 has a corrugated pattern formed of a plurality of corrugated units 14. In the annular body 11, the plurality of corrugated units 14 is connected along the annular direction CD. As shown in FIG. 3, the corrugated unit 14 includes a first stem 15, a second stem 16, a third stem 17, a first top portion 18, and the second top portion 19. The first stem 15 is a stem arranged substantially parallel with the axial direction LD. The second stem 16 is a stem arranged substantially parallel with the annular direction CD. The stent 10 of the first embodiment is configured such that the annular direction CD of the annular body 11 is inclined with respect to the radial direction RD by the angle +θ when the stent 10 is viewed in the radial direction RD perpendicular to the axial direction LD. In the form in which the annular body 11 is inclined with respect to the radial direction RD by the angle +θ, the sum of the length L1 of the first stem 15 of the corrugated unit 14 and the length L2 of the second stem 16 of the corrugated unit 14 is longer than the length L3 of the third stem 17.

As shown in FIG. 3, a first end portion 15a of the first stem 15 on one side (first side) and a first end portion 16a of the second stem 16 on one side (first side) are coupled to each other through the first top portion 18. A second end portion 16b of the second stem 16 on the other side (second side) and a first end portion 17a of the third stem 17 on one side (first side) are coupled to each other through the second top portion 19. A second end portion 17b of the third stem 17 on the other side (second side) is connected to a second end portion 15b of the first stem 15 on the other side (second side) in the corrugated unit 14 adjacent to such a second end portion 17b in the annular direction CD (a direction about an axis).

In a certain corrugated unit 14, a second top portion 19 coupling a second stem 16 and a third stem 17 to each other is not coupled to any of corrugated units 14 adjacent to the certain corrugated unit 14 in the annular direction CD. A third stem 17 of a certain corrugated unit 14 and a first stem 15 of a corrugated unit 14 adjacent to the certain corrugated unit 14 in the direction about the axis are, at end portions (a second end portion 17b and a second end portion 15b) thereof, coupled to each other to form a slit S therebetween. As shown in FIG. 3, the stent 10 of the first embodiment is configured such that adjacent two of the corrugated units 14 in the axial direction LD and two of the connection elements (described later) connecting these two corrugated units 14 in the axial direction LD form the cell. This cell basically has a closed cell structure, but in each corrugated unit 14, the second top portion 19 is a substantially V-shaped free end. Thus, the stent 10 of the first embodiment is formed such that the closed cell structure partially has an open cell structure. As described later, when the diameter of the stent 10 is expanded, the second stem 16 and the third stem 17 deform in a separation direction about the second top portion 19 as the free end.

As shown in FIG. 2, the plurality of connection elements 12 is arranged at equal intervals along the annular direction CD of the annular body 11. Each connection element 12 extends in a spiral shape about the center axis. As shown in FIG. 3, a first end portion 12a of a certain connection element 12 on one side (first side) is connected to a first top portion 18 of one corrugated unit 14 adjacent to the certain connection element 12 in the axial direction LD. That is, the first end portion 12a of the connection element 12 is, at a first top portion 18 of the corrugated unit 14a, connected to a first end portion 15a of a first stem 15 and a first end portion 16a of a second stem 16. Moreover, a second end portion 12b of the certain connection element 12 on the other side (second side) is connected to a second end portion 17b of a third stem 17 of the other corrugated unit 14b adjacent to the certain connection element 12 in the axial direction LD and a second end portion 15b of a first stem 15 of a corrugated unit 14c adjacent to the corrugated unit 14b in the direction about the axis. Note that in FIG. 3, reference numerals "14a", "14b", and "14c" are assigned to some of the corrugated units 14 for the sake of description above.

A direction in which the second top portion 19 of the corrugated unit 14 protrudes in the stent 10 of the first embodiment will be described herein. FIG. 5A is the view virtually showing the entirety of the stent 10 opened in the planar shape. In FIG. 5A, when the stent 10 is viewed from a practitioner operating the catheter (not shown) housing the stent 10, a side close to the practitioner in the axial direction LD of the stent 10 is taken as a proximal side LD1 and a side distant from the practitioner is taken as a distal side LD2. Moreover, in FIG. 5A, the annular bodies 11 and the connection elements 12 are drawn in a simple manner.

The stent 10 is implanted in the hollow organ such as a blood vessel, but in some cases, may be reimplanted elsewhere. In this case, the stent 10 is housed again in the catheter. In FIG. 5A, a direction in which the stent 10 is housed again is a direction from the distal side LD2 toward the proximal side LD1. FIG. 5B is an enlarged view of a portion from the center to an end portion on the proximal side LD1 in the axial direction LD of the stent 10. Moreover, FIG. 5C is an enlarged view of a portion from the center to an end portion on the distal side LD2 in the axial direction LD of the stent 10.

As shown in FIGS. 5B and 5C, in any of the corrugated units 14 forming the annular body 11 of the stent 10, the second top portion 19 is formed to protrude to the distal side LD2 in the direction (from LD2 toward LD1) of insertion of the stent 10 into the catheter. According to the above-described configuration, when the stent 10 is housed again in the catheter, the substantially V-shaped protruding end of the second top portion 19 as the free end does not face an insertion port of the catheter, and therefore, the stent 10 can be easily housed again in the catheter.

Figure 6:
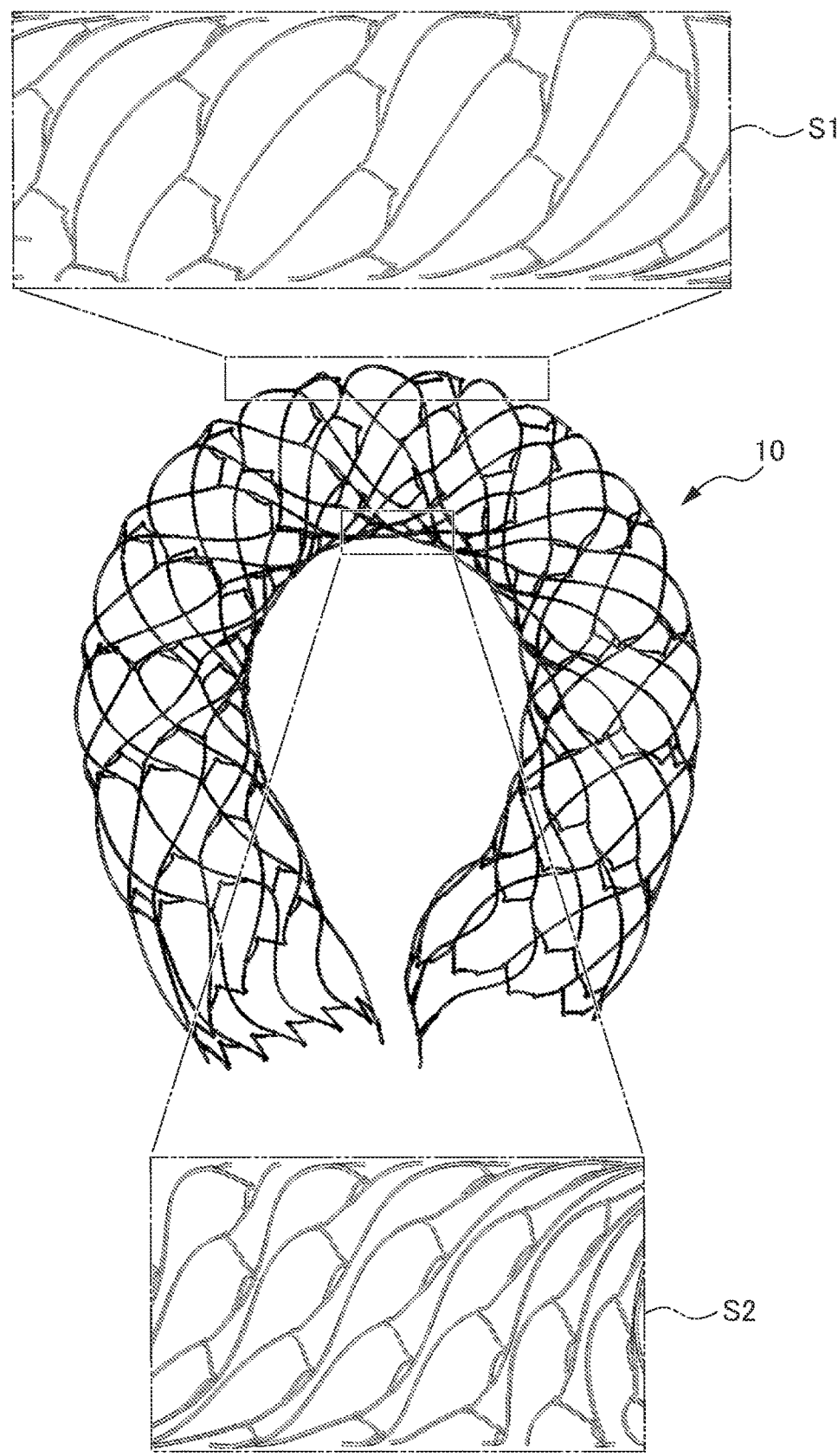
FIG. 6 is a view showing the shape of each portion in a case where the diameter-expanded stent 10 is bent in a substantially U-shape.
Figure 7:
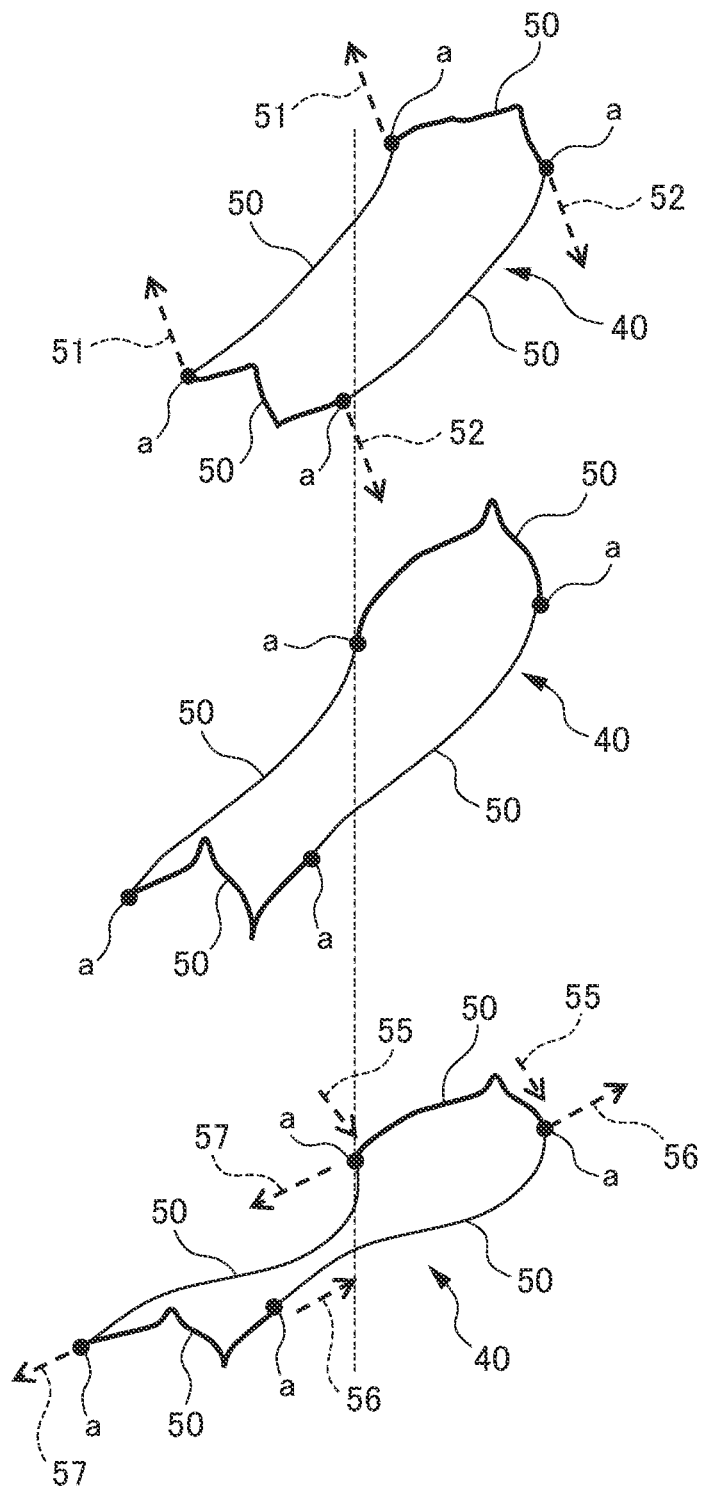
FIG. 7 is a schematic view showing the state of cells 40 in each region of the stent 10 when the stent 10 is virtually opened in the planar shape.
Figure 8:
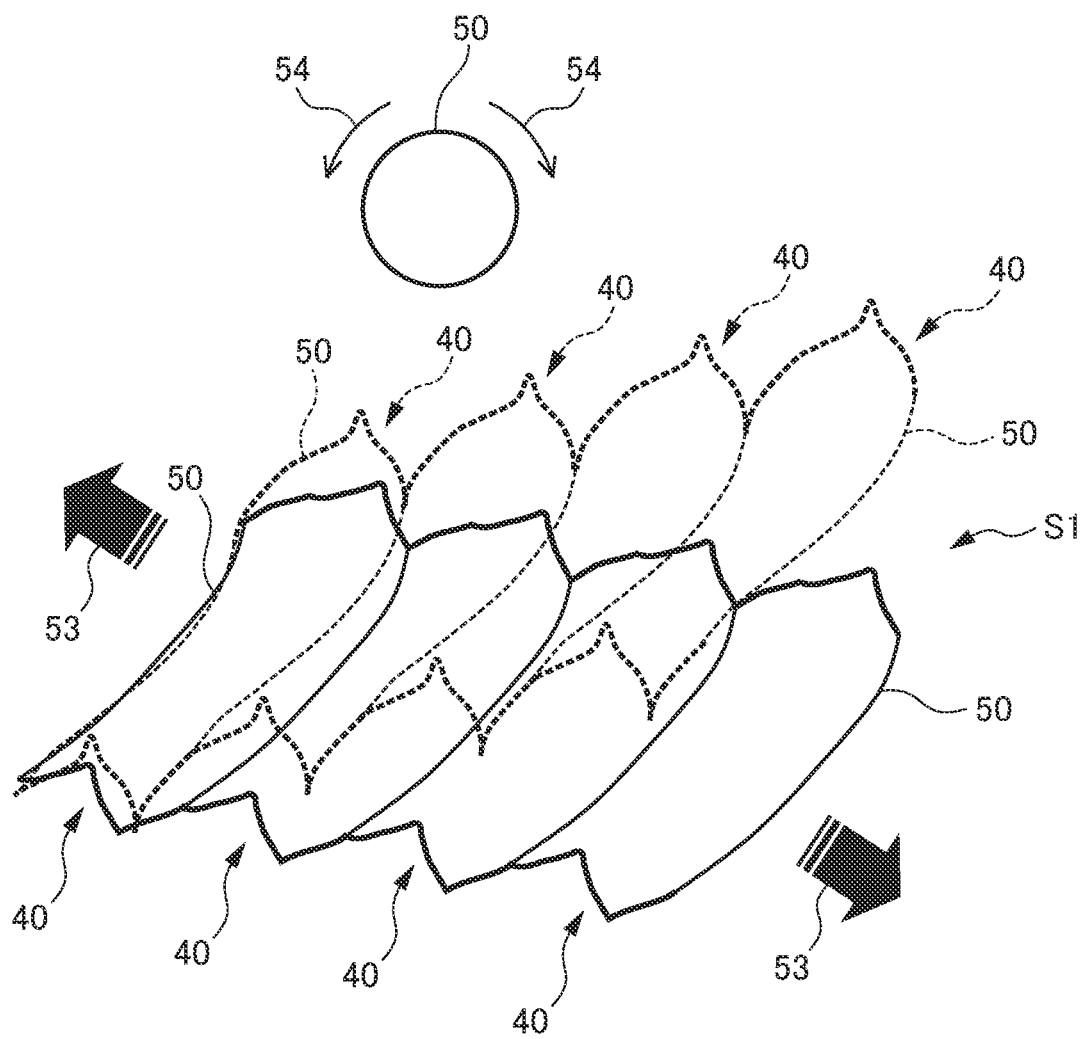
FIG. 8 is a schematic view showing the state of continuous cells 40 in a region S1 of the bent stent 10 when the stent 10 is virtually opened in the planar shape.

Next, patency when the stent 10 of the first embodiment is bent will be described. FIG. 6 is a view showing the shape of each portion in a case where the diameter-expanded stent 10 (see FIG. 4A) is bent in a substantially U-shape. FIG. 7 is a schematic view showing the state of a cell 40 in each region of the stent 10 shown in FIG. 6 when the stent 10 is virtually opened in the planar shape. FIG. 7 shows, at the center thereof, the cell 40 in a no-load state (the state of FIG. 4A) in which any of tensile force and compression force does not act on the cell 40. FIG. 8 is a schematic view showing the state of continuous cells 40 in a region S1 of the bent stent 10 shown in FIG. 6 when the stent 10 is virtually opened in the planar shape. FIG. 8 schematically shows, on an upper side therein, the section of a strut 50 by a circle. This circle is drawn for describing stress acting on one strut 50, and is different from an actual strut section.

As shown in FIG. 6, when the diameter-expanded stent 10 is bent in the substantially U-shape, the cells 40 are pulled in the region S1 on a back side (outside) of the bent portion. In this state, stress acting on the region S1 is, as shown on an upper side in FIG. 7, in the directions of arrows 51, 52 at each connection point a between the struts 50 forming the cell 40. Thus, as shown in FIG. 8, the continuous cells 40 in the region S1 deform so as to be pulled in the directions of arrows 53. That is, in FIG. 8, the struts 50 of the cells 40 in the no-load state as indicated by dotted lines deform (move) so as to be pulled in the directions of the arrows 53 as indicated by solid lines. In this state, when the strut 50 is viewed in section, the strut 50 deforms so as to rotate in two directions indicated by arrows 54, as shown on the upper side in FIG. 8. The directions indicated by the arrows 54 on the upper side in FIG. 8 correspond to the directions of the arrows 53 on a lower side in FIG. 8.

On the other hand, in FIG. 6, the cells 40 are compressed in a region S2 on a stomach side (inside) of the bent portion. In this state, stress acting on the region S2 is, as shown on a lower side in FIG. 7, in the directions of arrows 55 to 57 at each connection point a between the struts 50 forming the cell 40. Thus, although not shown in the figure, the continuous cells 40 in the region S2 deform so as to be pulled in a direction in which an interval between the struts 50 is narrowed.

Figure 9:
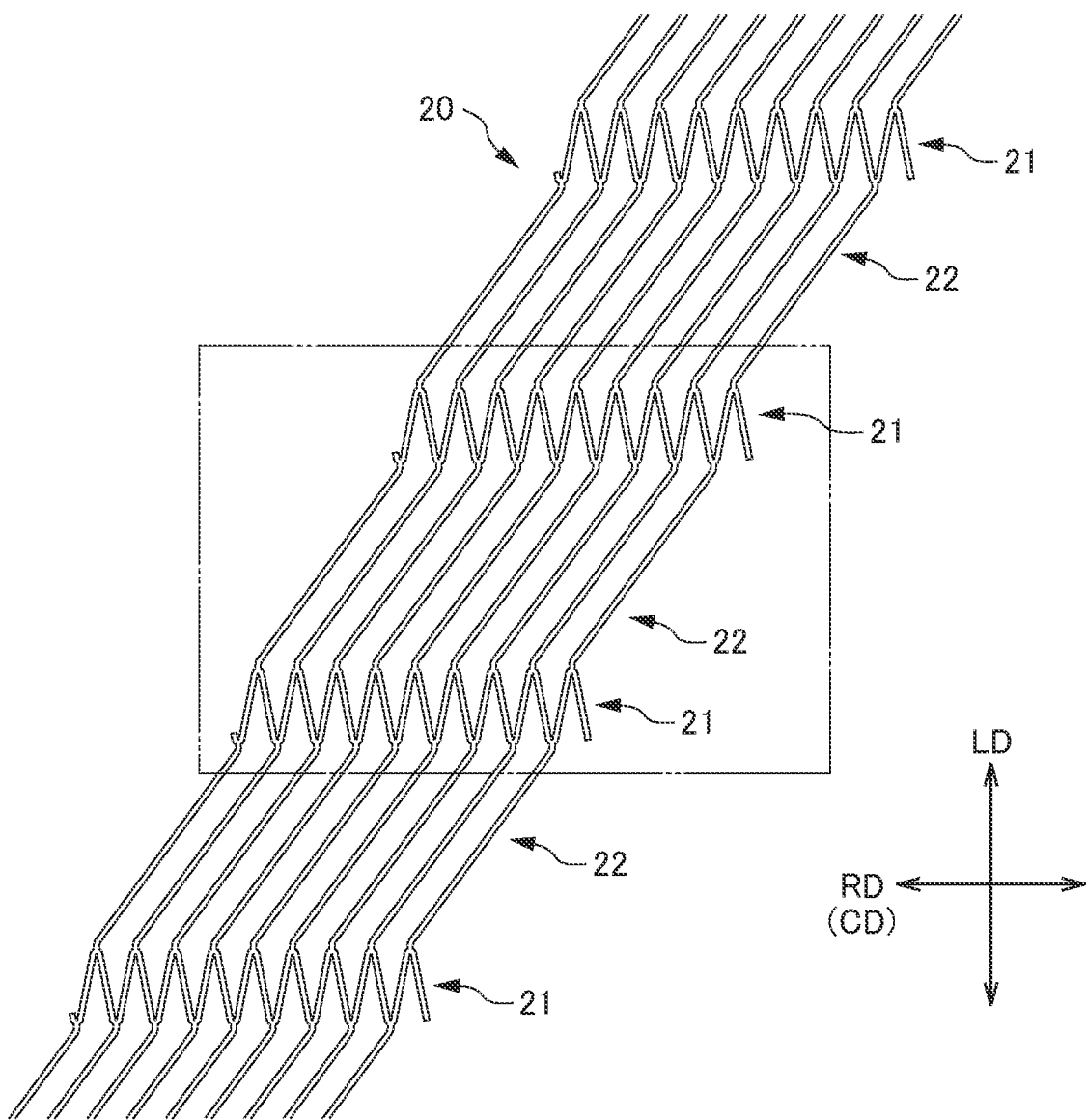
FIG. 9 is a development view showing a state in which a stent 20 of Comparative Example 1 is virtually opened in a planar shape.
Figure 10:
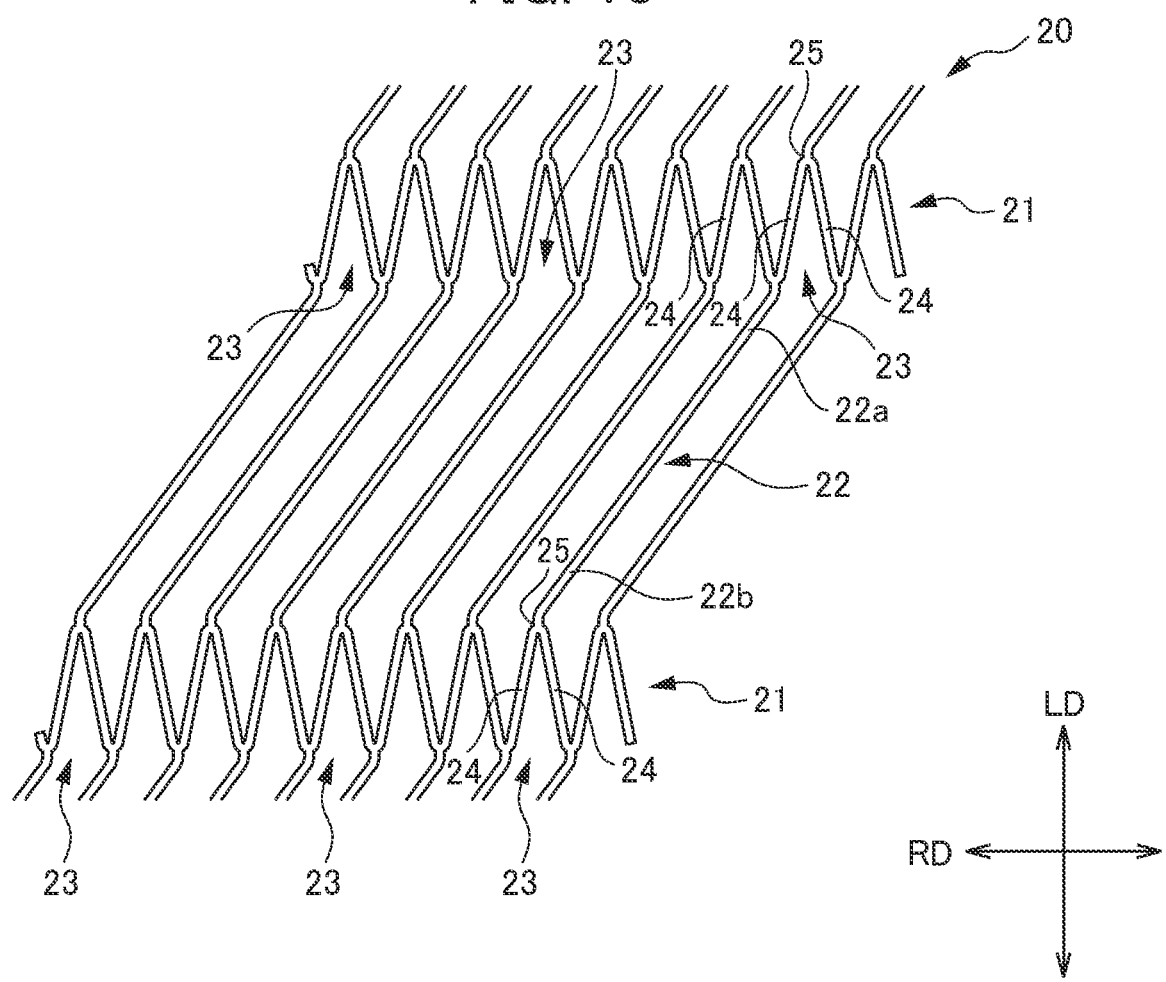
FIG. 10 is a partially-enlarged view of the stent 20.
Figure 11:
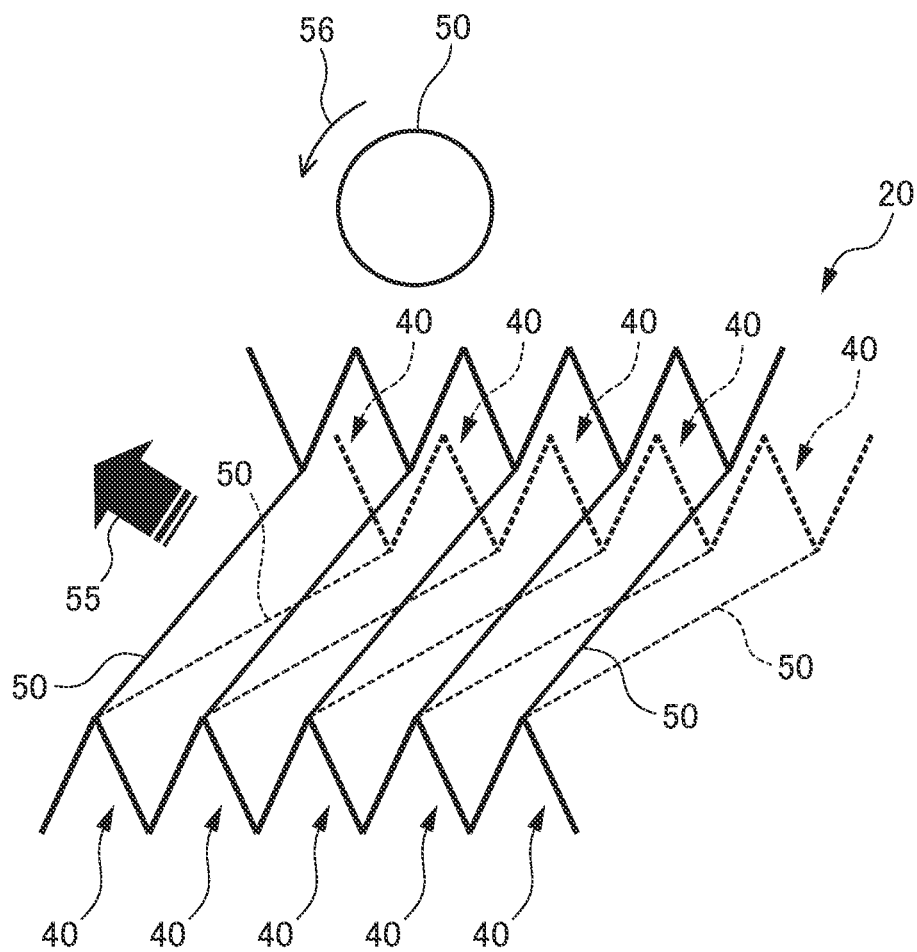
FIG. 11 is a schematic view showing the state of continuous cells 40 in a back-side region of the bent stent 20 when the stent 20 is virtually opened in the planar shape.

Next, deformation in response to stress on each of the stents of Comparative Example 1, Comparative Example 2, and the first embodiment will be described. FIG. 9 is a development view showing a state in which a stent 20 of Comparative Example 1 is virtually opened in a planar shape. FIG. 10 is a partially-enlarged view of the stent 20 shown in FIG. 9. FIG. 11 is a schematic view showing the state of continuous cells 40 in a back-side region of the bent stent 20 when the stent 20 is virtually opened in the planar shape. FIG. 11 is the schematic view showing the state of the continuous cells 40 in the back-side region of the bent stent 20 of Comparative Example 1 when the stent 20 is virtually opened in the planar shape.

As shown in FIG. 9, the stent 20 of Comparative Example 1 includes a plurality of annular bodies 21 arranged next to each other in the axial direction LD and connection elements 22 connecting the annular bodies 21 adjacent to each other in the axial direction LD. When the stent 20 of Comparative Example 1 is viewed in the radial direction RD perpendicular to the axial direction LD, an annular direction CD of the annular body 21 is substantially coincident with the radial direction RD.

As shown in FIG. 10, the stent 20 of Comparative Example 1 has a corrugated pattern formed such that a plurality of substantially V-shaped elements 23 is connected in the circumferential direction. The V-shaped element 23 is formed such that two stems 24 are coupled to each other at a top portion 25. The V-shaped elements 23 are configured such that the top portions 25 thereof face in the same direction in the axial direction LD, and the stems 24 of adjacent ones of the V-shaped elements 23 in the circumferential direction are connected to each other to form the corrugated pattern.

Two end portions 22a, 22b of each connection element 22 in a longitudinal direction thereof are each connected to adjacent two of the V-shaped elements 23 in the axial direction LD. The end portion 22a of the connection element 22 on one side (first side) is connected in the axial direction LD to the stems 24 of adjacent two of the V-shaped elements 23 in a direction along the corrugated pattern. Moreover, the end portion 22b of the connection element 22 on the other side (second side) is connected to the top portion 25 of the V-shaped element 23 adjacent to the above-described two V-shaped elements 23 in the axial direction LD. As described above, in the stent 20 of Comparative Example 1, all of the top portions 25 are connected to the connection elements 22. Thus, the stent 20 of Comparative Example 1 has a closed cell structure with no free end.

The diameter of the stent 20 of Comparative Example 1 is expanded as in the stent 10 (see FIG. 4) of the embodiment. When the stent 20 is bent in a substantially U-shape, the cells 40 are pulled in the back-side region. In this state, the continuous cells 40 in the back-side region deform diagonally in the direction of an arrow 55 as shown in FIG. 11. That is, in FIG. 11, struts 50 of the cells 40 in a no-load state as indicated by dotted lines deform (move) as indicated by solid lines. In this state, when the strut 50 is viewed in section, the strut 50 deforms so as to rotate in one direction indicated by an arrow 56, as shown on an upper side in FIG. 11.

The direction indicated by the arrow 56 on the upper side in FIG. 11 corresponds to the direction indicated by the arrow 55 on a lower side in FIG. 11. As described above, in the stent 20 of Comparative Example 1, deformation of the cell 40 is small in the back-side region of the bent portion, and the direction of deformation when the strut 50 is viewed in section is only one direction. Thus, in the stent 20 of Comparative Example 1, the amount of deformation for absorbing stress acting on the back-side region is smaller than that in the stent 10 of the embodiment. That is, in the stent 20 of Comparative Example 1, a twist/bend easily occurs in the back-side region due to stress acting on the bent portion. The same also applies to a stomach-side region of the bent portion in the stent 20 of Comparative Example 1, and the stent 20 of Comparative Example 1 has such a structure that a twist/bend easily occurs due to the stress acting on the bent portion.

Figure 12:
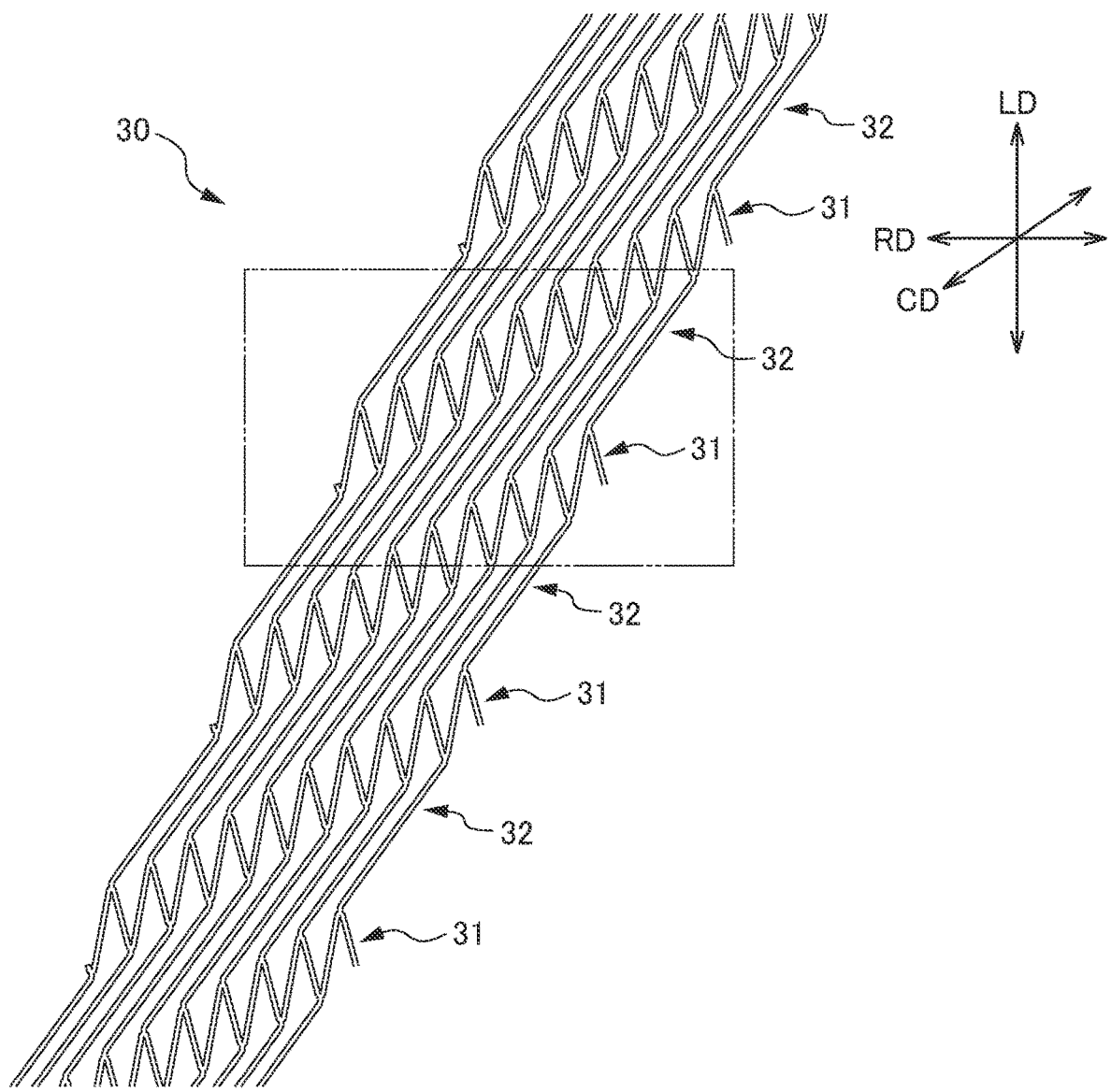
FIG. 12 is a development view showing a state in which a stent 30 of Comparative Example 2 is virtually opened in a planar shape.
Figure 13:
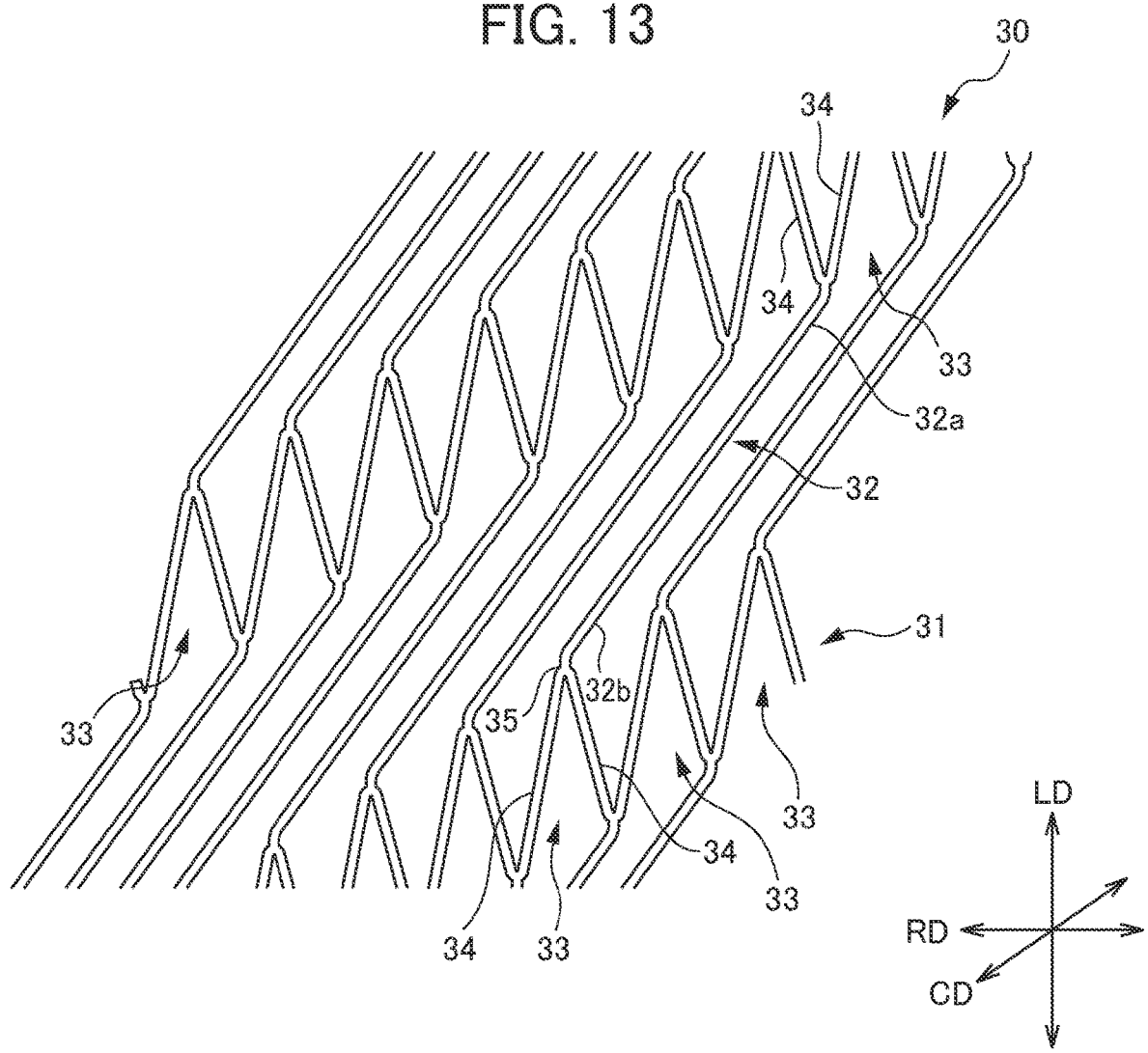
FIG. 13 is a partially-enlarged view of the stent 30.

FIG. 12 is a development view showing a state in which a stent 30 of Comparative Example 2 is virtually opened in a planar shape. FIG. 13 is a partially-enlarged view of the stent 30 shown in FIG. 12. FIG. 14 is a schematic view showing the state of continuous cells 40 in a back-side region of the bent stent 30 when the stent 30 is virtually opened in the planar shape.

As shown in FIG. 12, the stent 30 of Comparative Example 2 includes a plurality of annular bodies 31 arranged next to each other in the axial direction LD and connection elements 32 connecting the annular bodies 31 adjacent to each other in the axial direction LD. When the stent 30 of Comparative Example 2 is viewed in the radial direction RD perpendicular to the axial direction LD, the annular direction CD of the annular body 31 is inclined with respect to the radial direction RD.

As shown in FIG. 13, the stent 30 of Comparative Example 2 has a corrugated pattern formed such that a plurality of substantially V-shaped elements 33 is connected in the annular direction CD. The V-shaped element 33 is formed such that two stems 34 are coupled to each other at a top portion 35. The V-shaped elements 33 are configured such that the top portions 35 thereof face in the same direction in the axial direction LD, and the stems 34 of adjacent ones of the V-shaped elements 33 in the annular direction CD are connected to each other to form the corrugated pattern.

Two end portions 32a, 32b of each connection element 32 in a longitudinal direction thereof are each connected to adjacent two of the V-shaped elements 33 in the axial direction LD. The end portion 32a of the connection element 32 on one side (first side) is connected in the axial direction LD to the stems 34 of adjacent two of the V-shaped elements 33 in a direction along the corrugated pattern extending along the annular direction CD. Moreover, the end portion 32b of the connection element 32 on the other side (second side) is connected to the top portion 35 of the V-shaped element 33 adjacent to the above-described two V-shaped elements 33 in the axial direction LD. As described above, in the stent 30 of Comparative Example 2, all of the top portions 35 are connected to the connection elements 32. Thus, the stent 30 of Comparative Example 2 has a closed cell structure with no free end.

The diameter of the stent 30 of Comparative Example 2 is expanded as in the stent 10 (see FIG. 4A) of the embodiment. When the stent 30 is bent in a substantially U-shape, the cells are pulled in the back-side region. In this state, the continuous cells in the back-side region deform diagonally in the direction of an arrow 57 as shown in FIG. 14. That is, in FIG. 14, struts 50 of the cells in a no-load state as indicated by dotted lines deform (move) as indicated by solid lines. In this state, when the strut 50 is viewed in section, the strut 50 deforms so as to rotate in one direction indicated by an arrow 58, as shown on an upper side in FIG. 14.

The direction indicated by the arrow 58 on the upper side in FIG. 14 corresponds to the direction indicated by the arrow 57 on a lower side in FIG. 14. As described above, in the stent 30 of Comparative Example 2, deformation of the cell is small in the back-side region of the bent portion, and the direction of deformation when the strut 50 is viewed in section is only one direction. Thus, in the stent 30 of Comparative Example 2, the amount of deformation for absorbing stress acting on the back-side region is smaller than that in the stent 10 of the embodiment. That is, in the stent 30 of Comparative Example 2, a twist/bend easily occurs in the back-side region due to stress acting on the bent portion. The same also applies to a stomach-side region of the bent portion in the stent 30 of Comparative Example 2, and the stent 30 of Comparative Example 2 has such a structure that a twist/bend easily occurs due to the stress acting on the bent portion.

Figure 15A:
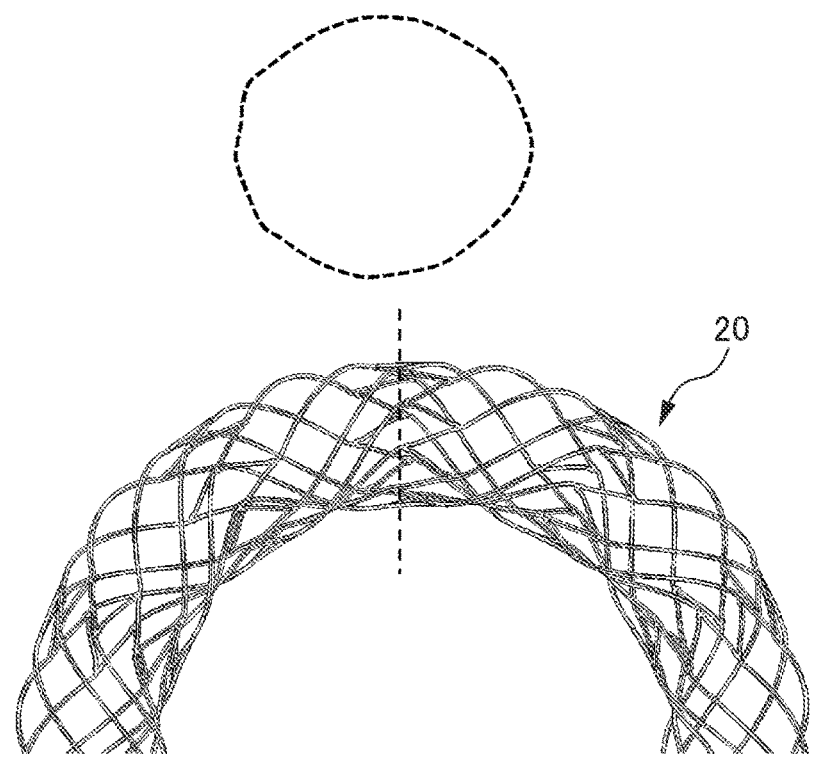
FIG. 15A is a view for describing the patency of the stent 30 of Comparative Example 1.
Figure 15B:
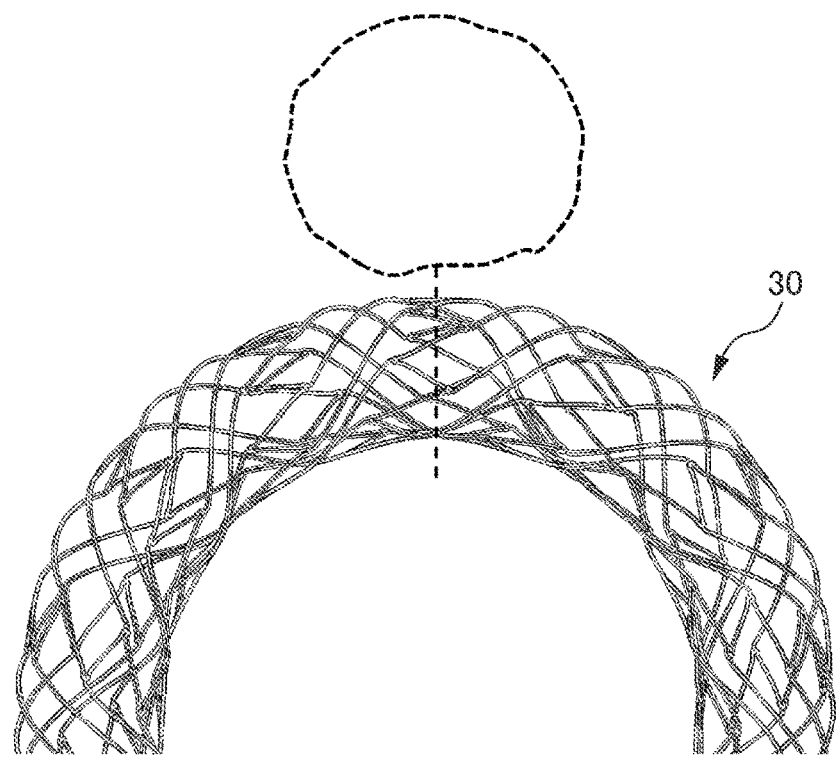
FIG. 15B is a view for describing the patency of the stent 30 of Comparative Example 2.
Figure 15C:
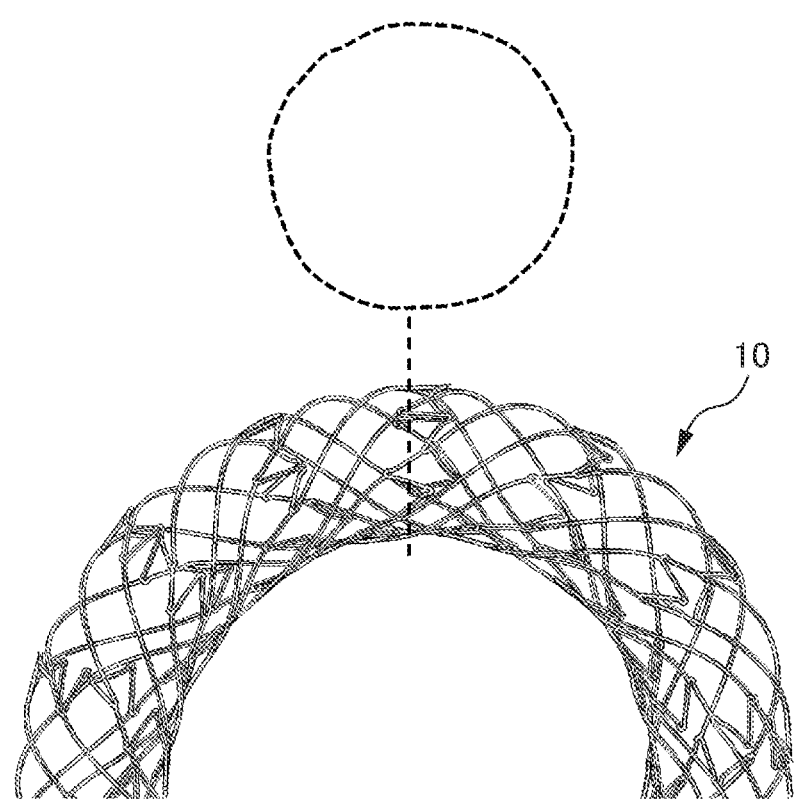
FIG. 15C is a view for describing the patency of the stent 30 of the embodiment.

Next, the patency of each of the stents of Comparative Example 1, Comparative Example 2, and the embodiment will be described. FIGS. 15A to 15C are views for describing the patency of each of the stents of Comparative Example 1, Comparative Example 2, and the embodiment. FIGS. 15A to 15C show sectional shapes when the diameters of the stents of Comparative Example 1, Comparative Example 2, and the embodiment are expanded to the same diameter and these stents are bent in a substantially U-shape. On an upper side in FIGS. 15A to 15C, the sectional shape at a center portion of a bend indicated by a dashed line is shown. On a lower side in FIGS. 15A to 15C, an appearance when the stent is bent in the substantially U-shape is shown.

It has been found that in each of the stent 20 of Comparative Example 1 as shown in FIG. 15A and the stent 30 of Comparative Example 2 as shown in FIG. 15B, a kink leading to the twist/bend of the section in a substantially oval shape occurs and the patency against bending is low. This is because each cell deforms only in one direction in response to the stress caused by bending in the stent 20 of Comparative Example 1 and the stent 30 of Comparative Example 2. On the other hand, it has been found that in the stent 10 of the embodiment as shown in FIG. 15C, the twist/bend of the section is less likely to occur and the patency against bending is high. This is because each cell deforms in two directions in response to the stress caused by bending in the stent 10 of the embodiment.

As described above, the stent 10 of the first embodiment includes the free ends (the second top portions 19) in the plurality of corrugated units 14 forming the corrugated pattern. Thus, two stems connected to the free end move in the separation direction when the stent 10 is bent, and therefore, the cells can be entirely deformed in two directions. Thus, the stent 10 of the embodiment has a high patency against bending.

The stent 10 of the first embodiment is formed such that the second top portions 19 as the free ends protrude to the distal side in the direction of insertion into the catheter. According to the present configuration, the substantially V-shaped protruding ends of the second top portions 19 as the free ends do not face the insertion port of the catheter when the stent 10 is housed in the catheter again, and therefore, the stent 10 can be easily housed in the catheter again.

In the stent 10 of the first embodiment, a third stem 17 of a certain corrugated unit 14 and a first stem 15 of a corrugated unit 14 adjacent to the certain corrugated unit 14 in the direction about the axis are, at end portions thereof, coupled to each other to form a slit S therebetween. Thus, in the stent 10 of the first embodiment, the third stem 17 coupled to the first stem 15 and the second stem 16 coupled to such a third stem 17 at the second top portion 19 can be more greatly deformed.

Second Embodiment

Next, a stent 10A of a second embodiment will be described. In description and drawings for the second embodiment, the same reference numerals as those of the first embodiment are used to represent members etc. equivalent to those of the first embodiment, and overlapping description thereof will be omitted.

Figure 16:
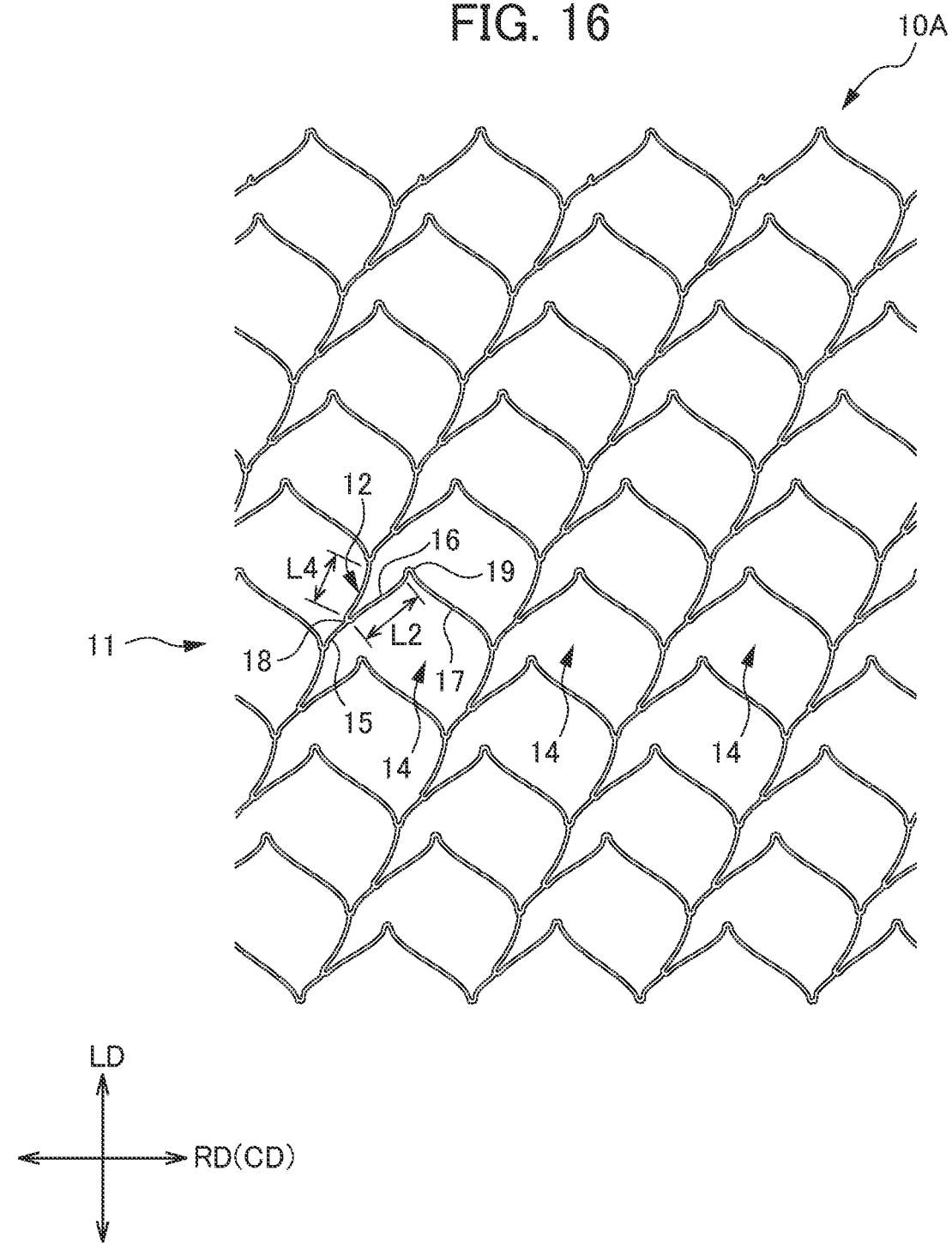
FIG. 16 is a development view showing a state in which a stent 10A of a second embodiment is virtually opened in a planar shape.
Figure 17:
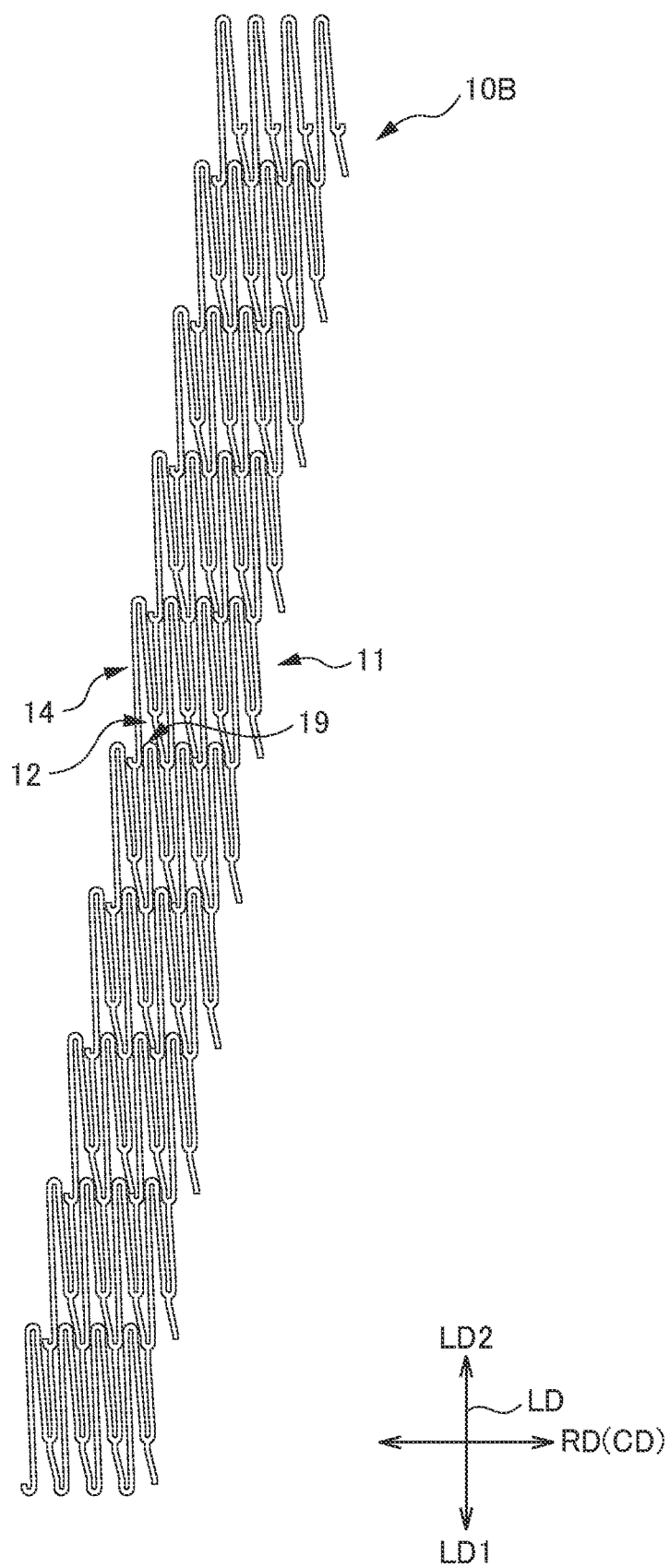
FIG. 17 is a development view showing a state in which the diameter of the stent 10A is narrowed.
Figure 18:
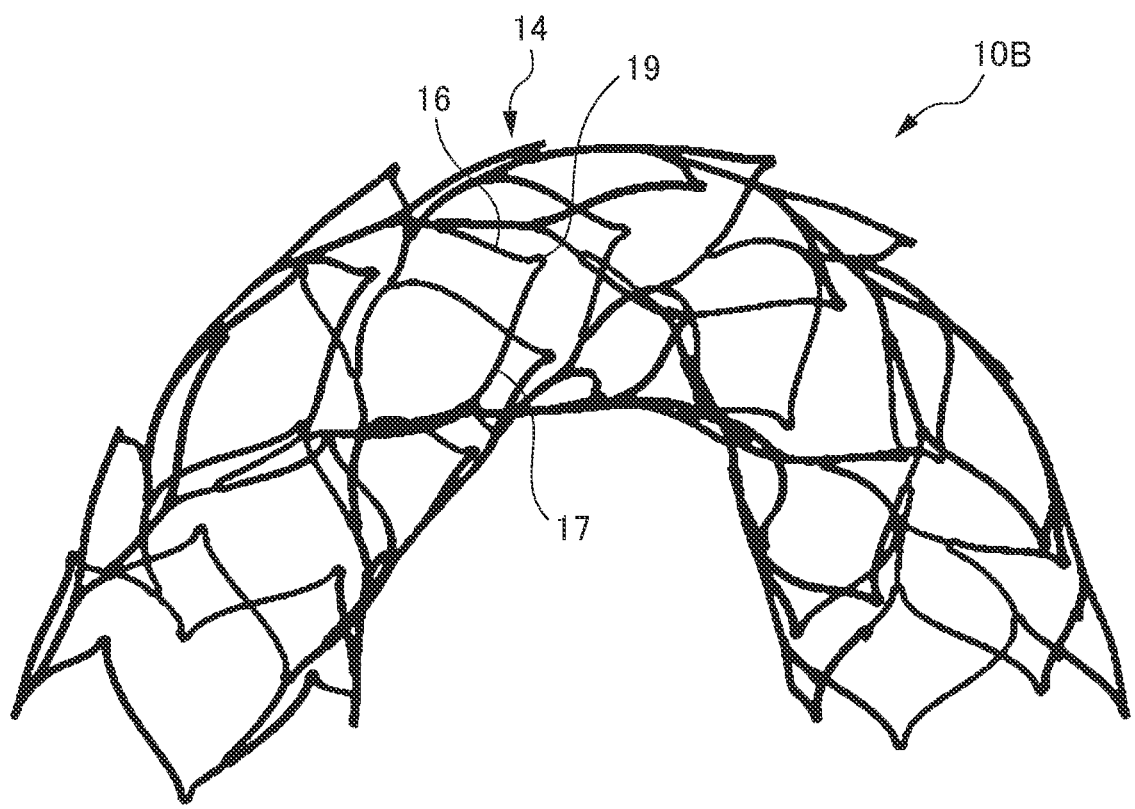
FIG. 18 is a view showing a shape in a case where the diameter-expanded stent 10A is bent in a substantially U-shape.

FIG. 16 is a development view showing a state in which the stent 10A of the second embodiment is virtually opened in a planar shape. FIG. 17 is a development view showing a state in which the diameter of the stent 10A is narrowed. FIG. 18 is a view showing a shape in a case where the diameter-expanded stent 10A is bent in a substantially U-shape.

As shown in FIG. 16, in the stent 10A of the second embodiment, the length L4 of a connection element 12 is set shorter than the length L2 of a second stem 16. Specifically, the length L4 of the connection element 12 is set to, e.g., about 0.7 to 0.9 in terms of the value of L4/L2. The length L4 of the connection element 12 and the length L2 of the second stem 16 are measured in terms of the shortest distance (a straight-line distance).

In the stent 10A of the second embodiment, a plurality of corrugated units 14 is connected along a radial direction RD. That is, when the stent 10A of the second embodiment is viewed in the radial direction RD perpendicular to an axial direction LD, an annular direction CD of an annular body 11 is substantially coincident with the radial direction RD.

In the stent 10A of the second embodiment, the length L4 of the connection element 12 is set shorter than the length L2 of the second stem 16. According to the present configuration, an interval between adjacent ones of the corrugated units 14 in the axial direction LD is short, and therefore, the number of corrugated units 14 per unit length in the axial direction LD can be increased. As the number of corrugated units 14 increases as described above, a surface area per unit length in the axial direction LD increases. Thus, blood vessel holding performance of the stent 10A can be improved.

In the stent 10A of the second embodiment, the plurality of corrugated units 14 is connected along the radial direction RD. Thus, upon processing of the stent, stress acting on the inside of a strut is uniformly transmitted in the radial direction RD at the step of expanding the diameter of a laser-processed thin tube to a finishing diameter. In a case where the stress acting on the inside of the strut is uniformly transmitted in the radial direction RD as described above, e.g., the twist of the strut due to non-uniform local stress is less likely to occur, and therefore, a more-uniform expanded shape can be obtained in a circumferential direction. Moreover, in the stent 10A of the second embodiment, the plurality of corrugated units 14 can be patterned along the radial direction RD, leading to excellent workability.

In the stent 10A of the second embodiment, a basic structure of the corrugated unit 14 is the same as that of the first embodiment. That is, as shown in FIG. 17, any of the corrugated units 14 is formed such that a substantially V-shaped protruding end of a second top portion 19 protrudes to a distal side LD2 in the direction (from LD2 toward LD1) of insertion of the stent 10A into a catheter (not shown). Thus, the stent 10A of the second embodiment can be also easily housed in the catheter again, as in the first embodiment. Moreover, in the stent 10A of the second embodiment, the second top portion 19 is less likely to overlap with the connection element 12 while being compressed radially as shown in FIG. 17, and therefore, upon diameter expansion, the stent 10A can be more uniformly deployed.

Note that two stems 16, 17 connected to the second top portion 19 as a free end move in a separation direction when the stent 10A of the second embodiment is bent in the substantially U-shape as shown in FIG. 18, and therefore, cells can be entirely deformed in two directions. Thus, the stent 10A has a high patency against bending.

The embodiments of the stent according to the present invention have been described above, but the present disclosure is not limited to the above-described embodiments. Various modifications and changes as in later-described variations can be made, and are also included in the technical scope of the present disclosure. Moreover, most preferred advantageous effects of the present disclosure have been merely described as the advantageous effects of the embodiments, and the present disclosure is not limited to those described in the embodiments. Note that the above-described embodiments and the later-described variations may be used in combination as necessary, but detailed description thereof will be omitted.

Figure 19:
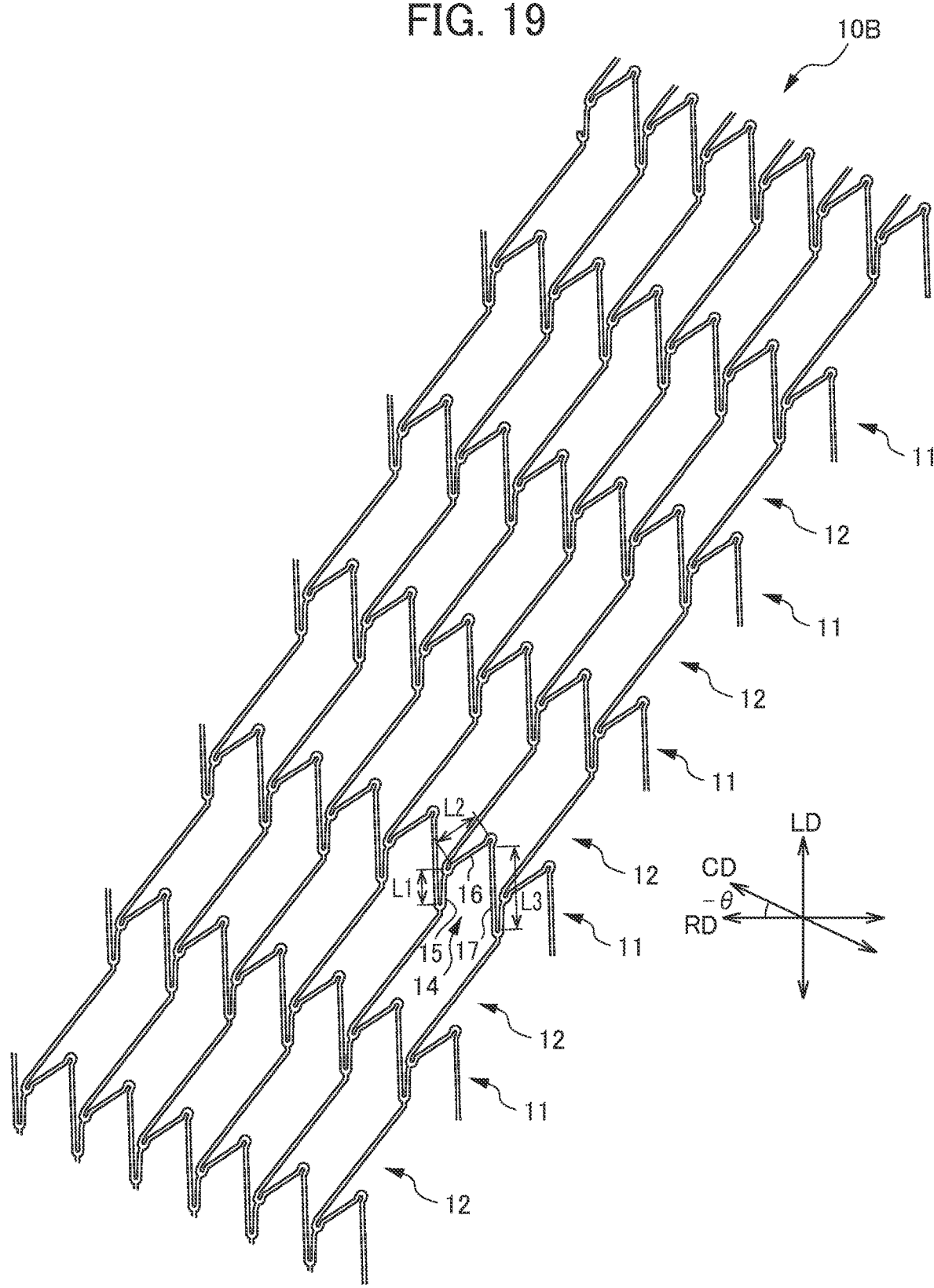
FIG. 19 is a development view showing a state in which a stent 10A of a first variation is virtually opened in a planar shape.

FIG. 19 is a development view showing a state in which a stent 10B of a first variation is virtually opened in a planar shape. The stent 10B of the first variation is different from the stent 10 of the first embodiment in the direction of inclination of an annular direction CD of an annular body 11 with respect to a radial direction RD. Specifically, when the stent 10B of the first variation is viewed in the radial direction RD perpendicular to an axial direction LD, the annular direction CD of the annular body 11 is inclined with respect to the radial direction RD by an angle −θ. In the form in which the annular body 11 is inclined with respect to the radial direction RD by the angle −θ as shown in FIG. 19, the sum of the length L1 of a first stem 15 of a corrugated unit 14 and the length L2 of a second stem 16 of the corrugated unit 14 is shorter than the length L3 of a third stem 17. As shown in FIG. 19, the direction of inclination of the annular direction CD of the annular body 11 with respect to the radial direction RD may be opposite to that of the stent 10 (see FIG. 2) of the first embodiment. In the present configuration, advantageous effects similar to those of the stent 10 of the first embodiment can be obtained. Note that the configuration of the first variation can be also applied to the stent 10A of the second embodiment.

Figure 20A:
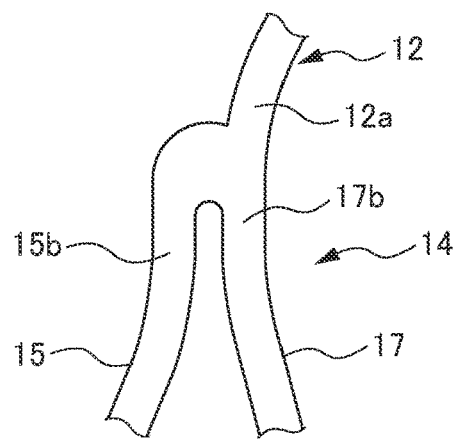
FIG. 20A is a partially-enlarged view of a corrugated unit 14 of a second variation.
Figure 20B:
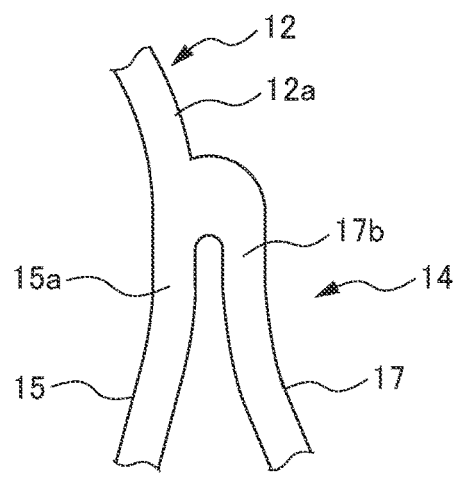
FIG. 20B is a partially-enlarged view of the corrugated unit 14 of the second variation.
Figure 20C:
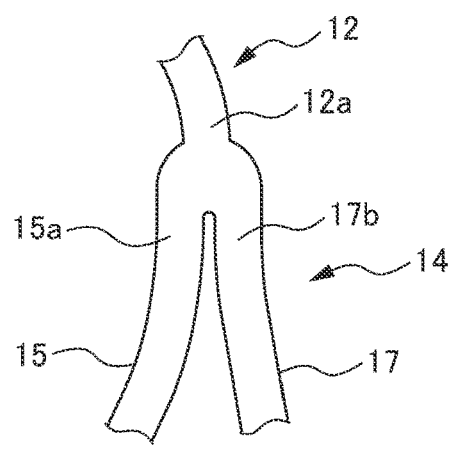
FIG. 20C is a partially-enlarged view of the corrugated unit 14 of the second variation.

FIGS. 20A to 20C are partially-enlarged views of a corrugated unit 14 of a second variation. In the first and second embodiments, connection shapes as shown in FIGS. 20A to 20C can be applied to the connection portion between the connection element 12 and the corrugated unit 14. FIGS. 20A to 20C show the shapes applicable to the connection portion in any of a region A1 or a region A2 of the corrugated unit 14 shown in FIG. 2. Hereinafter, the connection portion in the region A1 of FIG. 2 will be described as an example. The region A1 is a portion at which the first end portion 12a of the connection element 12 is connected to the second end portion 15b of the first stem 15 of the corrugated unit 14 and the second end portion 17b of the third stem 17 of the corrugated unit 14.

In the connection shape shown in FIG. 20A, the first end portion 12a of the connection element 12 is connected to a side close to the second end portion 17b of the third stem 17.

In the connection shape shown in FIG. 20B, the first end portion 12a of the connection element 12 is connected to a side close to the second end portion 15b of the first stem 15. In the connection shape shown in FIG. 20C, the first end portion 12a of the connection element 12 is connected to between the second end portion 15b of the first stem 15 and the second end portion 17b of the third stem 17. The connection shape shown in each figure for the second variation can be selected as necessary according to transmission of force upon bending of the stent and the state of stress acting on the inside and surface of the stent, for example.

Figure 21:
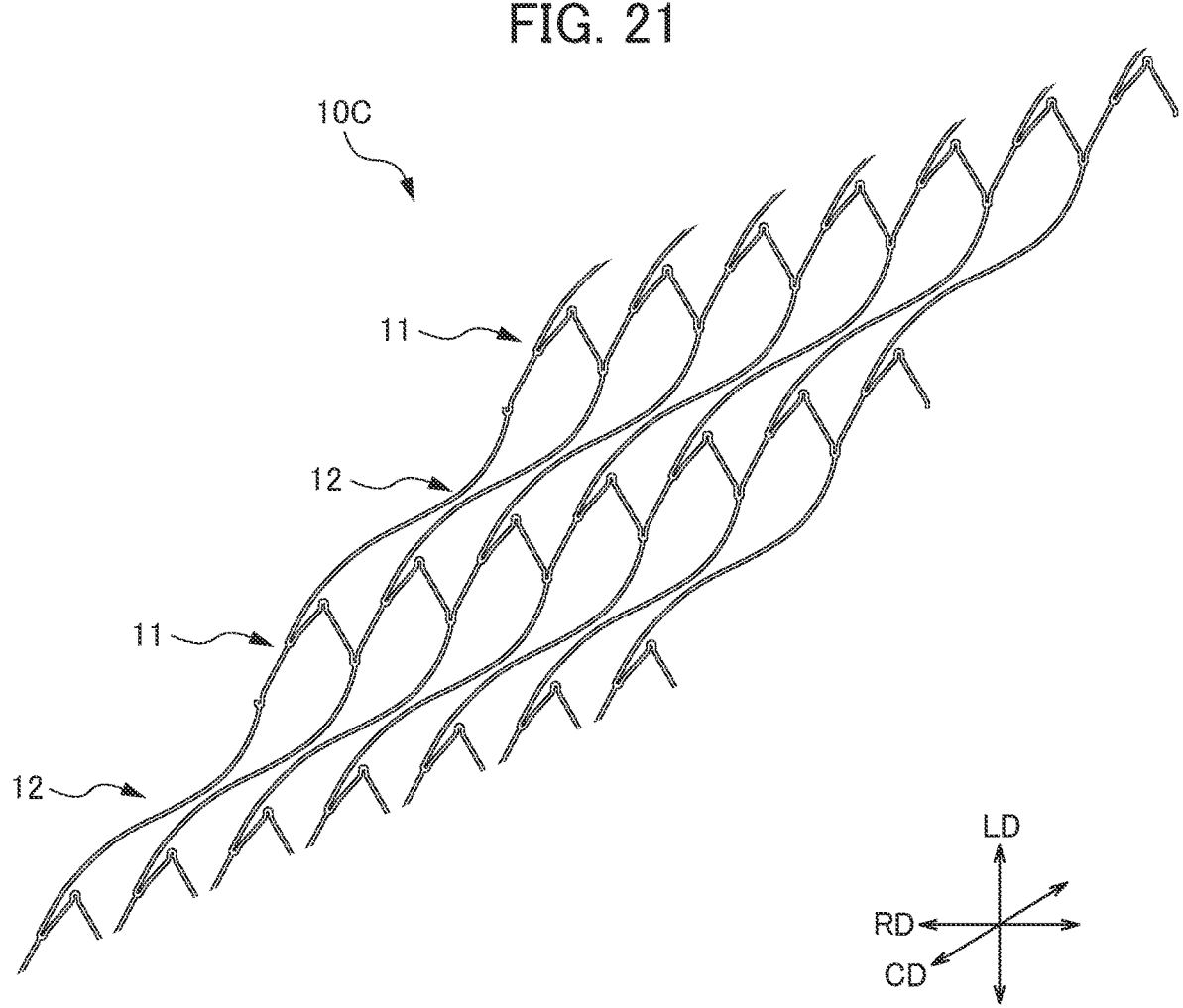
FIG. 21 is a development view showing a first configuration of a stent 10C of a third variation.
Figure 22:
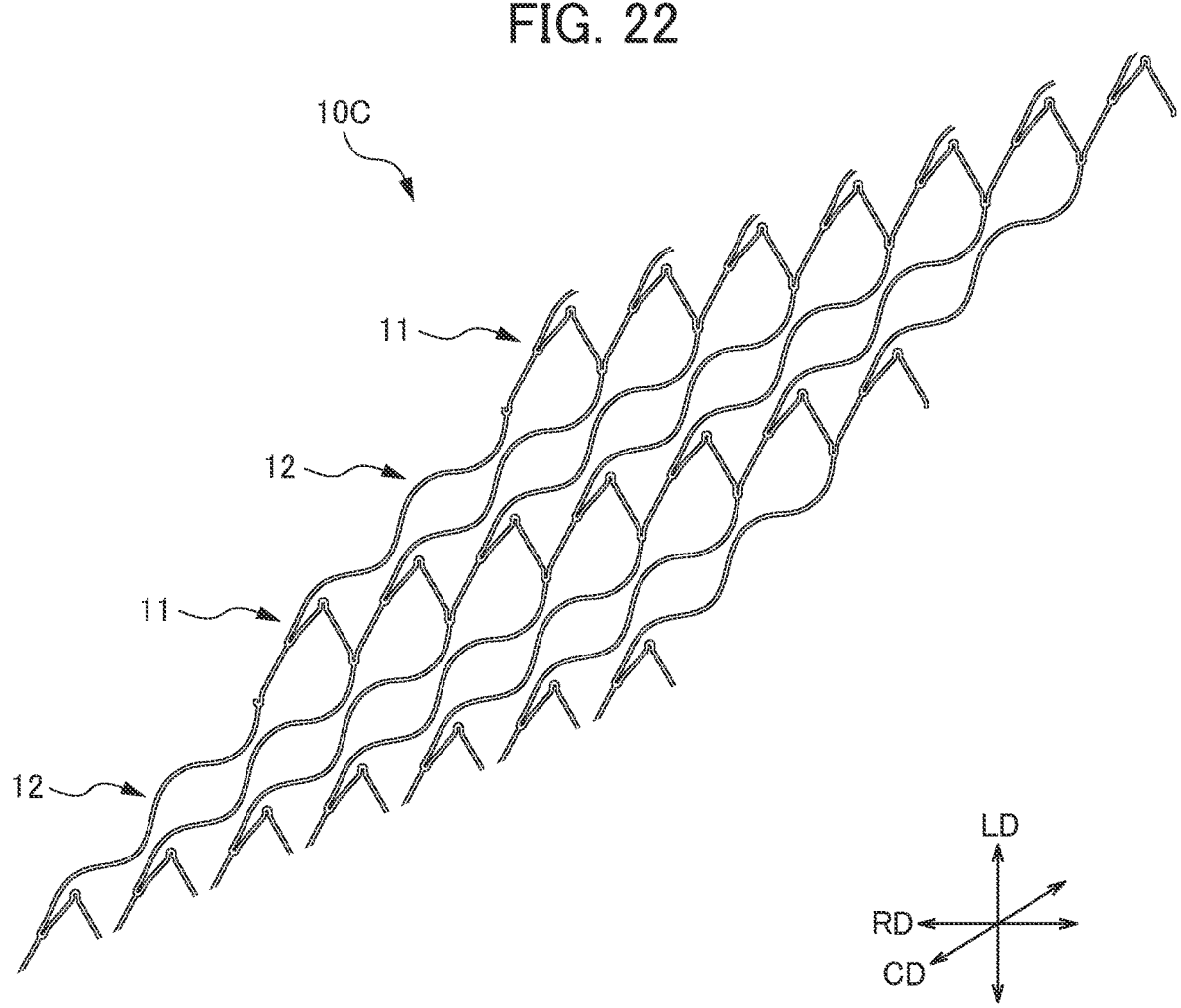
FIG. 22 is a development view showing a second configuration of the stent 10C of the third variation.

FIGS. 21 and 22 are development views showing a state in which a stent 10C of a third variation is virtually opened in a planar shape. FIG. 21 is the development view showing a first configuration of the stent 10C of the third variation. As shown in FIG. 21, in the first configuration of the stent 10C of the third variation, a connection element 12 connecting adjacent ones of annular bodies 11 in an axial direction LD is formed in a substantially S-shaped corrugated pattern. FIG. 22 is the development view showing a second configuration of the stent 10C of the third variation. As shown in FIG. 22, in the second configuration of the stent 10C of the third variation, the connection element 12 connecting adjacent ones of the annular bodies 11 in the axial direction LD is formed such that a substantially S-shaped corrugated pattern is repeated twice. In the connection element 12 of the second configuration, the substantially S-shaped corrugated pattern may be repeated three times or more. The shape of the connection element 12 shown in each figure for the third variation can be selected as necessary according to transmission of force upon bending of the stent and the state of stress acting on the inside and surface of the stent, for example.

Figure 23:
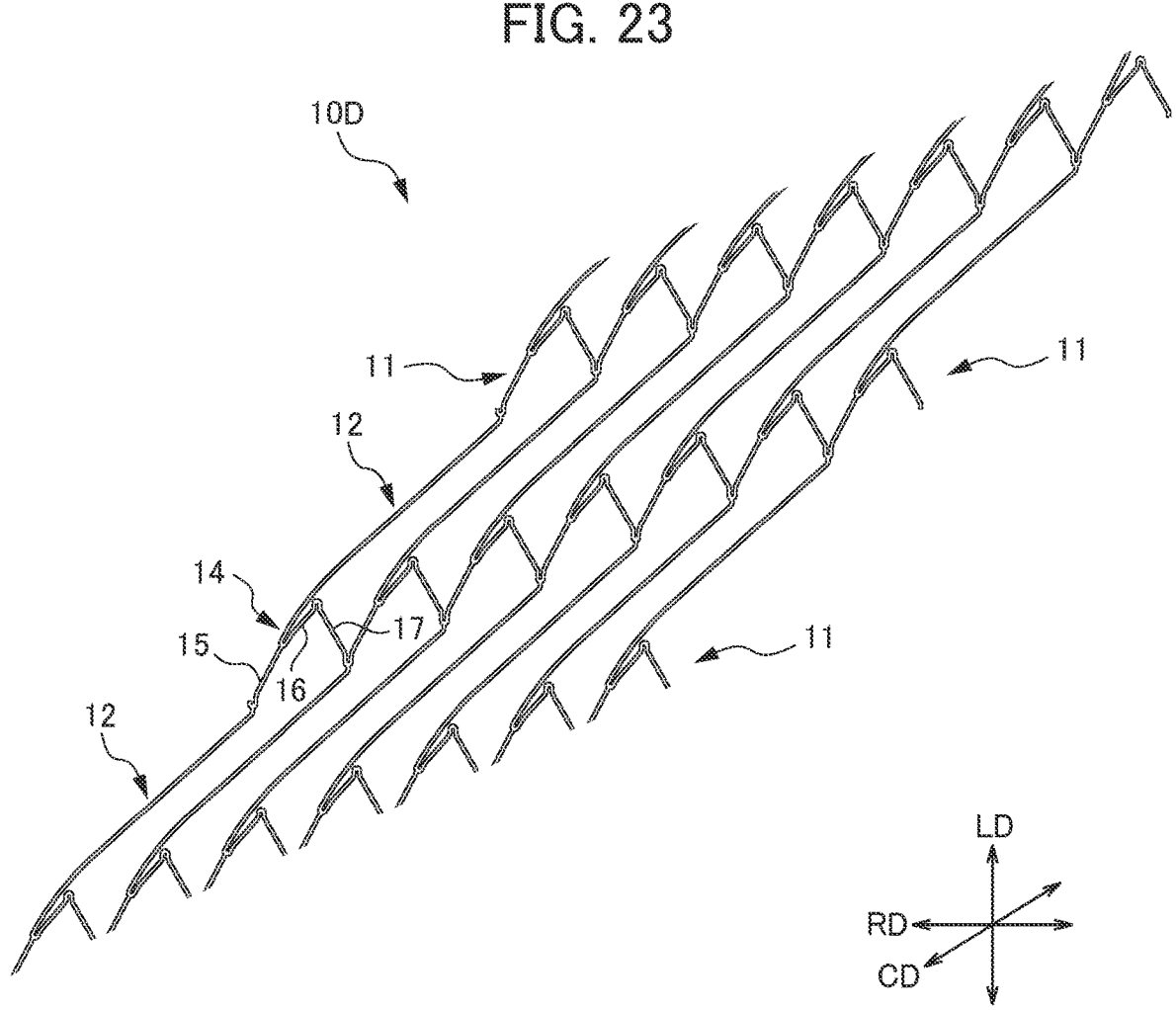
FIG. 23 is a development view showing a state in which a stent 10D of a fourth variation is virtually opened in a planar shape.

FIG. 23 is a development view showing a state in which a stent 10D of a fourth variation is virtually opened in a planar shape. As shown in FIG. 23, a first stem 15, a second stem 16, and a third stem 17 forming a corrugated unit 14 may be different from a connection element 12 connecting annular bodies 11 to each other in a strut thickness (e.g., the maximum diameter). The stent 10D of FIG. 23 is an example where the thickness of the connection element 12 is thinner than the thicknesses of the first stem 15, the second stem 16, and the third stem 17 for further enhancing flexibility. The strut thickness in the first stem 15, the second stem 16, the third stem 17, and the connection element 12 can be selected as necessary according to transmission of force upon bending of the stent and the state of stress acting on the inside and surface of the stent, for example. Note that the example where the connection element 12 is formed thinner in the stent 10D of the fourth variation has been described, but the strut thickness may be changed for any one or more of the first stem 15, the second stem 16, the third stem 17, and the connection element 12.

Figure 24:
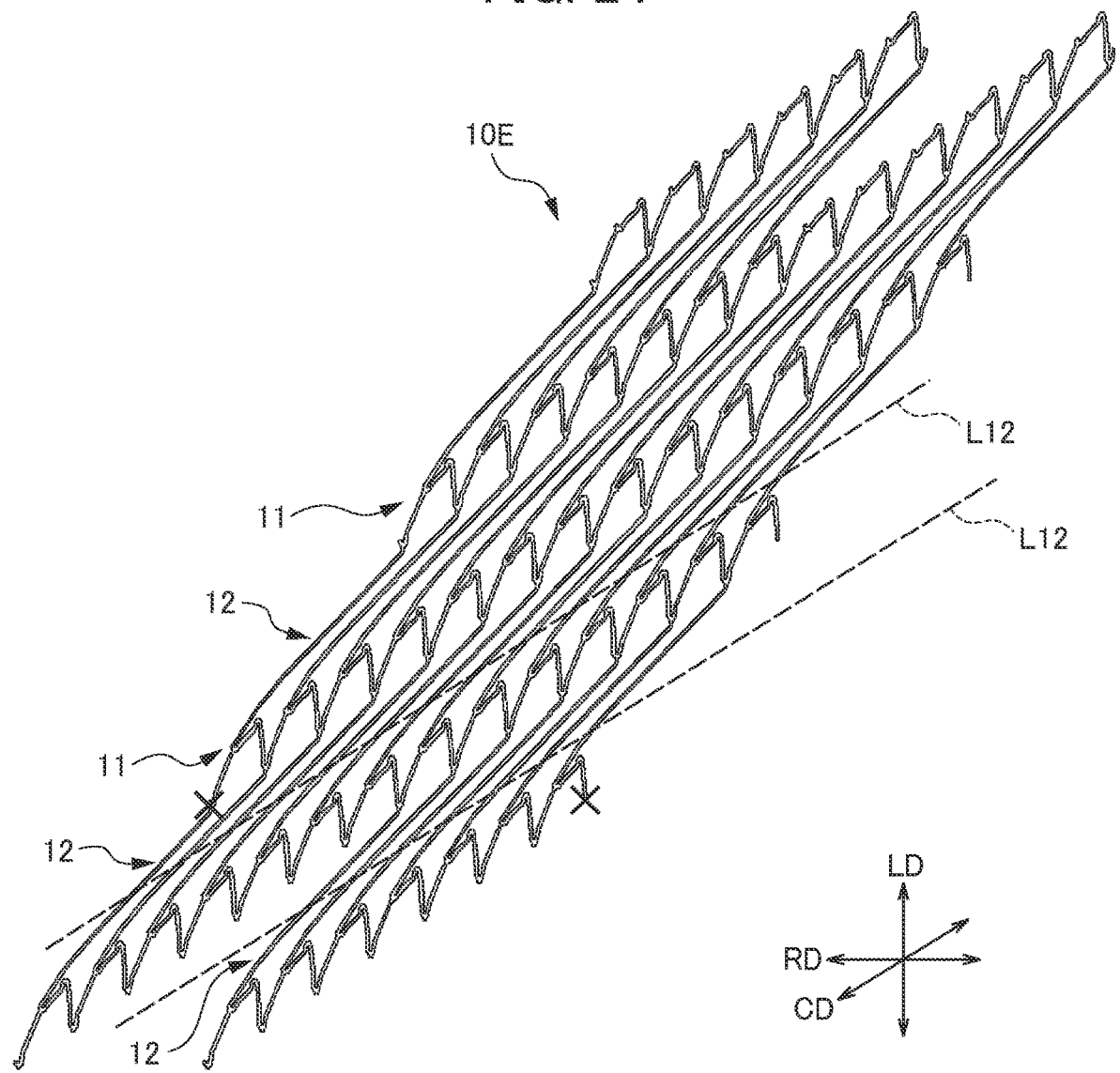
FIG. 24 is a development view showing a state in which a stent 10E of a fifth variation is virtually opened in a planar shape.

FIG. 24 is a development view showing a state in which a stent 10E of a fifth variation is virtually opened in a planar shape. As shown in FIG. 24, in the stent 10E of the fifth embodiment, two connection element bands L12 are provided between two connection points (cross marks) in a radial direction RD. In FIG. 24, these two connection points (the cross marks) indicate virtual connection positions in a circumferential direction of the substantially cylindrical stent 10D. The connection element band L12 indicates the line of a plurality of connection elements 12 arranged along an annular direction CD. In the stent 10E of the fifth variation, the two connection element bands L12 are provided between the two connection points (the cross marks) in the radial direction RD. Thus, as compared to a configuration (see, e.g., FIG. 2) in which a single connection element band L12 is provided between two connection points (cross marks) in the radial direction RD, the surface area and cell density of the stent 10E of the fifth variation can be increased. Note that in the stent 10E shown in FIG. 24, three or more connection element bands L12 may be provided between the two connection points (the cross marks) in the radial direction RD.

Figure 25:
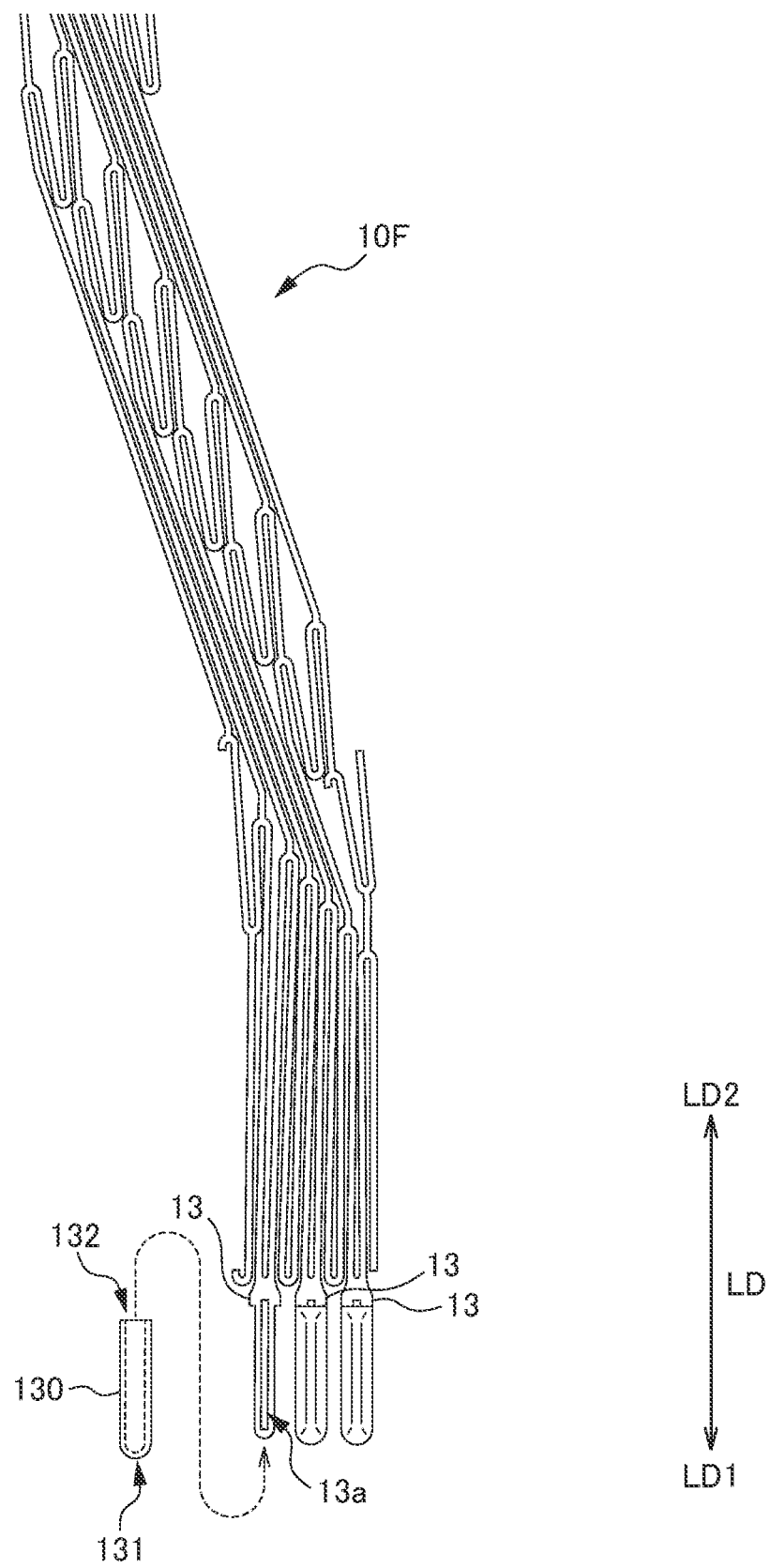
FIG. 25 is a development view showing a state in which a stent 10F of a sixth variation is virtually opened in a planar shape.

FIG. 25 is a development view showing a state in which a stent 10F of a sixth variation is virtually opened in a planar shape. FIG. 25 shows an area of the stent 10F from the substantially center to an end portion on a proximal side LD1 in an axial direction LD. As shown in FIG. 25, the stent 10F includes marker holding portions 13 at the end portion on the proximal side LD1. The marker holding portion 13 is a portion for holding a marker 130 (described later). Note that FIG. 25 shows an example where three marker holding portions 13 are provided at the end portion of the stent 10F on the proximal side LD1, but the number of marker holding portions 13 is not limited to that in the example of FIG. 25.

The marker holding portion 13 is configured such that a slit 13a is formed along a center portion of the marker holding portion 13 in a longitudinal direction thereof. The slit 13a is a portion to be fastened to a substantially center portion of the marker 130 by swaging. Note that a left one of the three marker holding portions 13 shown in FIG. 25 shows a state before fastening of the marker 130.

The marker 130 used for the stent 10F of the sixth variation is formed in a substantially cylindrical shape. Of the marker 130, one end portion is formed with a substantially semicircular head portion 131, and the other end portion is formed with an opening 132. In the marker 130 held on the proximal side LD1 of the stent 10F, the head portion 131 is positioned in an insertion direction (from LD2 toward LD1) when the stent 10F is housed in a catheter (not shown) again. As in the marker 100 (see FIG. 4B) described in the first embodiment, the marker 130 is made of a radiopaque material.

As shown in FIG. 25, the marker 130 is inserted onto the marker holding portion 13 of the stent 10F from an opening 132 side, and by swaging, the marker holding portion 13 of the stent 10F and the marker 130 can be fastened to each other. Although not shown in the figure, an area of the stent 10F from the substantially center to an end portion on a distal side LD2 in the axial direction LD is also configured similarly to FIG. 25.

According to the configuration of the sixth variation, the substantially semicircular head portion 131 is, when the stent 10F is housed in the catheter again, positioned on the side from which the marker 130 is inserted, and therefore, the stent 10F can be more easily housed in the catheter again.

EXPLANATION OF REFERENCE NUMERALS 10, 10A, 10B, 10C, 10D, 10E, 10F Stent
11 Annular Body (Corrugated Pattern Body)
12 Connection Element
12a First End Portion
12b Second End Portion
14 Corrugated Unit
15 First Stem
15a First End Portion
15b Second End Portion
16 Second Stem
16a First End Portion
16b Second End Portion 17 Third Stem
17a First End Portion
17b Second End Portion
18 First Top Portion
19 Second Top Portion
100 Marker

The invention claimed is:

1. A stent to be inserted into a catheter while being compressed radially, comprising:
a plurality of corrugated pattern bodies having a corrugated pattern and arranged next to each other in an axial direction; and
a plurality of connection elements arranged in a direction about an axis and connecting the corrugated pattern bodies adjacent to each other,
wherein the corrugated pattern is formed of a plurality of corrugated units, each corrugated unit includes a first stem, a second stem, a third stem, a first top portion coupling a first end portion of the first stem on one side and a first end portion of the second stem on one side, and a second top portion coupling a second end portion of the second stem on the other side and a first end portion of the third stem on one side, and a second end portion of the third stem on the other side is connected to a second end portion of the first stem on the other side in another one of the corrugated units adjacent to each corrugated unit in the direction about the axis,
the second top portion of each corrugated unit is formed to protrude only toward a distal side in a direction of insertion of the stent into the catheter, and
a first end portion of each connection element on one side is connected to the first top portion of one of adjacent ones of the corrugated units in the axial direction, and a second end portion of each connection element is connected to the second end portion of the first stem of the other one of the adjacent ones of the corrugated units in the axial direction.

2. The stent according to claim 1, wherein
the third stem of one of the corrugated units and the first stem of another one of the corrugated units adjacent to the one of the corrugated units in the direction about the axis are, at end portions thereof, coupled to each other to form a slit therebetween.

3. The stent according to claim 1, wherein
when viewed in a radial direction perpendicular to the axial direction, an annular direction of the corrugated pattern of each corrugated pattern body is inclined with respect to the radial direction.

4. The stent according to claim 3, wherein
a sum of a length of the first stem and a length of the second stem is longer than a length of the third stem.

5. The stent according to claim 3, wherein
a sum of a length of the first stem and a length of the second stem is shorter than a length of the third stem.

6. The stent according to claim 1, wherein
a length of each connection element is shorter than a length of the second stem, and
when viewed in a radial direction perpendicular to the axial direction, an annular direction of the corrugated pattern of each corrugated pattern body is substantially coincident with the radial direction.

* * * * *